US006368612B1

(12) United States Patent
Lanza et al.

(10) Patent No.: US 6,368,612 B1
(45) Date of Patent: Apr. 9, 2002

(54) DEVICES FOR CLOAKING TRANSPLANTED CELLS

(75) Inventors: Robert P. Lanza, Clinton; William Chick, Wellesley, both of MA (US)

(73) Assignee: Biohybrid Technologies LLC, Shrewsbury, MA (US)

( * ) Notice: Subject to any disclaimer, the term of this patent is extended or adjusted under 35 U.S.C. 154(b) by 0 days.

(21) Appl. No.: 08/998,263

(22) Filed: Dec. 24, 1997

Related U.S. Application Data

(60) Provisional application No. 60/069,382, filed on Dec. 12, 1997.

(51) Int. Cl.[7] ............................. A61F 2/00; A61F 13/00
(52) U.S. Cl. ....................... 424/422; 424/423; 424/424; 424/426; 604/891.1; 514/866
(58) Field of Search ................................. 424/422, 423, 424/424, 426; 604/891.1; 514/866

(56) References Cited

U.S. PATENT DOCUMENTS

| | | | |
|---|---|---|---|
| 4,352,883 A | 10/1982 | Lim | 435/178 |
| 4,409,331 A | 10/1983 | Lim | 435/178 |
| 4,663,286 A | 5/1987 | Tsang et al. | 435/178 |
| 5,084,350 A | 1/1992 | Chang et al. | 428/402.2 |
| 5,324,518 A | 6/1994 | Orth et al. | 424/423 |
| 5,427,935 A | 6/1995 | Wang et al. | 435/178 |
| 5,545,423 A | 8/1996 | Soon-Shiong et al. | 424/484 |
| 5,679,340 A | * 10/1997 | Chappel | 424/93.1 |
| 5,869,077 A | * 2/1999 | Dionne et al. | 424/422 |
| 5,871,767 A | 2/1999 | Dionne et al. | 424/422 |

FOREIGN PATENT DOCUMENTS

| | | |
|---|---|---|
| EP | 0 301 777 A1 | 7/1988 |
| WO | WO 95/19743 | 7/1995 |
| WO | WO 96/28029 | 9/1996 |

OTHER PUBLICATIONS

Cai et al., "Development and Evaluation of a System of Microencapsulation of Primary Rat Hepatocytes", Hepatology 10:855–860 (1989).
Soon–Shiong et al., "An Immunologic Basis for the Fibrotic Reaction to Implanted Microcapsules", Transplantation Proceedings 23:758–759 (1991).
Soon–Shiong et al., "Successful Reversal of Spontaneous Diabetes in Dogs by Intraperitoneal Microencapsulated Islets", Transplantation 54:769–774 (1992).
Villa et al., "Pharmacology of Lazaroids and Brain Energy Metabolism: A Review", Pharmacological Reviews 49:99–136 (1997).

* cited by examiner

*Primary Examiner*—Dwayne C. Jones
*Assistant Examiner*—C. Delacroix-Muirheid

(57) ABSTRACT

Implantable devices that include a source of a therapeutic substance and a capture agent are disclosed.

33 Claims, 2 Drawing Sheets

DEVICES FOR CLOAKING TRANSPLANTED CELLS

This application claims priority under 35 U.S.C. 119(e) to U.S. provisional application Ser. No. 60/069,382 entitled "Devices for Providing Therapeutic Substances," by Robert P. Lanza and William Chick, filed Dec. 12, 1997, the contents of which are hereby incorporated by reference.

The invention relates to inhibiting damage to donor tissue in a device in contact with a host tissue.

BACKGROUND OF THE INVENTION

Transplantation of donor tissue into a recipient can be used to treat a wide variety of disorders, including heart disease, neoplastic disease, and endocrine disease. The clinical application of transplantation-based therapies are, however, limited by several factors. These factors include immune rejection of transplanted allogeneic or xenogeneic tissue by the transplant recipient, a shortage of allogeneic donor-tissue, and donor-propagated immune attack of recipient tissue (graft-versus-host-disease).

Immune rejection of transplanted donor-tissue can be the most serious barrier to more widespread availability of the benefits of transplantation-based therapies. Implantation of allogeneic or xenogeneic donor-tissue into an immunocompetent recipient generally results in a vigorous and destructive immune response directed against the donor-graft. Efforts to prevent immune-based destruction of donor tissue have generally fallen into two categories. In one approach, efforts have been directed to moderating the recipient's immune response, e.g., by the induction of specific immunological tolerance to transplanted tissue, or much more frequently, by the administration of broad-spectrum immune suppressants, e.g., cyclosporin. In the other major approach, efforts to prolong the acceptance of a donor-graft have been directed to rendering the donor-graft less susceptible to attack, e.g., by immunoisolating the donor-tissue by encapsulating it in a way which minimizes contact of elements of the recipient's immune system with the encapsulated donor tissue.

Immunoisolation is particularly attractive for the treatment of endocrine disorders or in hormone or enzyme replacement therapies. For example, the implantation of immunoisolated pancreatic islet cells can be used to restore glucose-responsive insulin function in a diabetic recipient. Islets can be placed in a mechanical enclosure, or can be coated with a material, which allows relatively free diffusion of glucose, insulin, nutrients, and cellular waste products but which is impervious to components of the recipient's immune system.

SUMMARY OF THE INVENTION

A variety of devices can be used to contain or cloak a source of a therapeutic substance, often cells, which source provides the substance to a host or recipient subject. Such devices include implantable devices, of both the diffusion and perfusion types, and extra corporeal devices, e.g., those through which blood of the host or recipient is passed. In such devices, host molecules can attack the source of the therapeutic substance and impair the function of the device. Semipermiable components are used to inhibit the ability of host molecules to enter the device and attack the source of therapeutic substance. The inventors have discovered that release, by the device, of components of the source of therapeutic substance, can stimulate a host response against the device and that capture of such components, prior to release or prior to becoming available to the immune system of the host, can improve the performance of the device, e.g., by extending its useful lifetime.

The inventors have discovered that the inclusion in an implantable device of a capture agent, e.g., an antibody directed against an antigen of the source of a therapeutic substance, which sequesters therapeutic source molecules, can improve the performance of the device, e.g., by extending its useful lifetime.

Accordingly, the invention features, an implantable device which includes a source of a therapeutic substance, e.g., an islet, and a capture agent, e.g., an antibody which binds a component of the therapeutic substance, disposed within or on a semipermeable component. The capture agents are preferably immobilized within the interior of the device or on its surface or are in a different compartment than the source of a therapeutic substance, or otherwise immobilized to keep it from contacting the source of a therapeutic substance. The capture agent can, e.g., coupled to a substrate, e.g., an inert bead in a compartment of the microreactor, or can be coupled to the surface of the microreactor, or to the surface of a component of the microreactor.

In preferred embodiments, the capture agent is an antibody or antibody fragment, even more preferably, the capture agent is an antibody or antibody fragment which binds an antigen or epitope other than the therapeutic substance released by the source. In an even more preferred embodiment, the antibody or antibody fragment is directed against an antigen which is an MHC class I, an MHC class II, an SLA class I, or an SLA class II antigen. In another preferred embodiment, the antibody or antibody fragment is a human antibody, a humanized antibody, an antibody which is engineered to minimize host response, or an engineered binding protein of a parental protein which is preferably of human origin.

In preferred embodiments, the implantable device includes a cell or tissue. The cell or tissue can be autologous, allogeneic, or xenogeneic, with regard to the subject. A xenogeneic cell or tissue can be from a species which is concordant or discordant with the subject. The cell or tissue can be from the subject, but if it is from the subject, it is preferably genetically engineered to express a substance not normally expressed by or on that cell or tissue.

In preferred embodiments, the cell or tissue is from a dog, pig, goat, rabbit, horse, cow, or sheep, or a non-human primate species.

In preferred embodiments, the cell is a pancreatic islet cell. In preferred embodiments, the pancreatic islet is from a dog, pig, goat, rabbit goat, horse, cow, sheep, or a non-human primate. In particularly preferred embodiments, the pancreatic islet is from a pig. In preferred embodiments, the pancreatic islet is from a human other than the subject.

In preferred embodiments, the cell or tissue is genetically engineered.

The cell or tissue can be from the pancreas, adrenal gland, brain, kidney, liver, thymus parathyroid or thyroid. In a preferred embodiment, the cell is a cultured cell. In a preferred embodiment, the cell is from a primary culture. In a preferred embodiment, the cell has been treated with a cytokine or a growth factor.

In preferred embodiments, the cell is an immortalized cell; the cell is a blood cell; the cell or tissue is a fetal; the cell is a skin, astroglial, or myoblast cell.

In preferred embodiments, the source of a therapeutic substance (and preferably the capture agent) is immunoisolated from the host, e.g., it is isolated from contact with one or more host immune components, e.g., antibodies or components of the complement system.

In preferred embodiments, the implantable device is a perfusion device, e.g., devices through which the flow of blood is directed, e.g., intravascular devices, as e.g., in an arterial or venous shunt.

In preferred embodiments, the device can be a microcapsule or a macrocapsular device, e.g., a hollow fiber, a membrane chamber, or other device which separates the source of a therapeutic substance (and preferably the capture agent) from the host by an artificial semi-permeable barrier.

In preferred embodiments, the device serves to physically contain the source of a therapeutic substance, e.g., donor cells or tissues, (and preferably the capture agent), keeping them in a contained location, at least temporarily separated from the implantation site or tissues of the host.

In preferred embodiments, the device is a microcapsule or macrocapsule. It can include a gel member, e.g., a shape-retaining gel member, in which a source of a therapeutic substance, e.g., a cell or tissue, is embedded. The gel can be a hydrogel. In preferred embodiments, the hydrogel includes agarose, agar, collagen, polyethylene glycol (PEG), polyethylene oxide (PEO), or alginate. The agarose or alginate can have a high number of guluronic acid or a high number of mannuronic acid monomers. The microcapsule or macrocapsule can include a semipermeable membrane or coating, e.g., a semipermeable coating which surrounds a gel component, e.g. a gel core in which a cell or tissue is embedded. The semipermeable membrane can include a polymer, e.g., a positively charged polymer. By way of example, the positively charged polymer can be a polyamino acid. In preferred embodiments, the positively charged polymer includes lysine or ornithine. In a particularly preferred embodiment, the positively charged polymer is polylysine or another polymer of one or more positively charged amino acids. In preferred embodiments, the coating can include chitosan.

In another aspect, the invention features, a composite microreactor which includes:

(a) one, or a plurality, of an internal particle which includes:
  (i) a source of a therapeutic substance, e.g., an islet;
  (ii) an internal particle matrix, e.g., a gel core or a solid particle, which contacts the source;
  (iii) (optionally) an internal semipermeable particle coating enclosing the internal particle matrix; and
(b) a super matrix, e.g., a gel super matrix, in which the internal particle (or particles) is embedded; and
(c) (optionally) an outer semipermeable coating enclosing the super matrix, the composite microreactor preferably providing a molecular weight cutoff that prevents molecules larger than about 400,000 daltons from coming into contact with the source.

The composite microreactor includes one or more capture agents. The capture agent should be in a different compartment than the source of a therapeutic substance or otherwise immobilized to keep it from contacting the source of a therapeutic substance. The capture agent can, e.g., be coupled to the surface of a component or the microreactor.

In preferred embodiments, the capture agent is an antibody or antibody fragment, even more preferably, the capture agent is an antibody or antibody fragment which binds an antigen or epitope other than the therapeutic substance released by the source. In an even more preferred embodiment, the antibody or antibody fragment is directed against an antigen which is an MHC class I, an MHC class II, an SLA class I, or an SLA class II antigen. In another preferred embodiment, the antibody or antibody fragment is a human antibody, a humanized antibody, an antibody which is engineered to minimize host response, or an engineered binding protein of a parental protein which is preferably of human origin.

In preferred embodiments, a capture agent, e.g., an antibody which binds antigens or epitopes other than the therapeutic substance released by the source, is disposed within one or more of an internal particle or the super matrix.

In preferred embodiments, one compartment, e.g., an internal particle, can include a first capture agent and a second compartment, e.g., a second internal particle, or the super matrix can include a second capture agent.

A compartment can include two or more capture agents. A capture agent can be included in more than one compartment.

In preferred embodiments an internal particle is coated with the three-part composite layer described herein.

In another aspect, the invention features, a double composite microreactor which includes:

(1) one, or a plurality, of an internal particle which includes:
  (a) a source of a therapeutic substance, e.g., an islet;
  (b) an internal particle matrix which contacts the source; and
  (c) (optionally) an internal particle semipermeable coating enclosing the first internal particle matrix;
(2) one, or a plurality, of a particle which includes:
  (a) the internal particle or particles of (1)
  (b) a particle matrix in which the internal particle (or internal particles) is embedded; and
  (c) (optionally) a particle semipermeable coating enclosing the particle;
(3) a super matrix in which the particle (or particles) of (2) is embedded; and
(4) (optionally) a super matrix or outer semipermeable coating, e.g., of polylysine enclosing the super matrix.

The composite microreactor includes one or more capture agents. The capture agents should be in a different compartment than the source of a therapeutic substance, or otherwise immobilized to keep it from contacting the source of a therapeutic substance.

In preferred embodiments, the capture agent is an antibody or antibody fragment, even more preferably, the capture agent is an antibody or antibody fragment which binds an antigen or epitope other than the therapeutic substance released by the source. In an even more preferred embodiment, the antibody or antibody fragment is directed against an antigen which is an MHC class I, an MHC class II, an SLA class I, or an SLA class II antigen. In another preferred embodiment, the antibody or antibody fragment is a human antibody, a humanized antibody, an antibody which is engineered to minimize host response, or an engineered binding protein of a parental protein which is preferably of human origin.

In preferred embodiments, a capture agent, e.g., an antibody which binds antigens or epitopes other than the therapeutic substance released by the source, is disposed within one or more of an internal particle, a particle, or the super matrix.

A compartment can include two or more capture agents.

In a preferred embodiment, one compartment, e.g., an internal particle, can include a first capture agent and a second compartment, e.g., a second internal particle, or a particle, or the super matrix, can include a second capture agent.

A capture agent can be included in more than one compartment.

In preferred embodiments, an internal particle is coated with the three-part composite layer described herein; a particle is coated with the three-part composite layer described herein; an internal particle and a particle are coated with the three-part composite layer described herein; an internal particle does not include the three-part layer but a particle is coated with the three-part composite layer described herein.

In another aspect, the invention features, a composite microreactor which includes:

(a) one, or a plurality, of an internal particle which includes:
 (i) pig islet cells as a source of a therapeutic substance;
 (ii) an internal particle matrix of alginate;
 (iii) an internal semipermeable particle coating of low molecular wieght polylysine enclosing the internal particle matrix; and
(b) a super matrix of alginate in which the internal particle (or particles) is embedded; and
(c) an outer semipermeable coating of polylysine, e.g., low molecular weight polylysine, enclosing the super matrix, the composite microreactor preferably providing a molecular weight cutoff that prevents molecules larger than about 400,000 daltons from coming into contact with the source and having an antibody which reacts with a swine antigen, e.g., a SLA class I or class II antigen, as a capture agent attached to the outer coating of polylysine.

In preferred embodiments, the capture agent is an antibody or antibody fragment, even more preferably, the capture agent is an antibody or antibody fragment which binds an antigen or epitope other than the therapeutic substance released by the source. In an even more preferred embodiment, the antibody or antibody fragment is directed against an antigen which is an MHC class I, an MHC class II, an SLA class I, or an SLA class II antigen. In another preferred embodiment, the antibody or antibody fragment is a human antibody, a humanized antibody, an antibody which is engineered to minimize host response, or an engineered binding protein of a parental protein which is preferably of human origin.

In another aspect, the invention features, providing a subject with a therapeutic substance. The method includes implanting in the subject an implantable device which includes a source of a therapeutic substance and a capture agent, e.g., an implantable device described herein.

The inventors have discovered that the inclusion of a capture agent in an extracorporeal device can be used to protect a source of a therapeutic substance in the extracorporeal device and improve the performance of the device, e.g., by extending its useful lifetime.

Accordingly, the invention features, an extracorporeal device through which is passed a host fluid, e.g., blood. (After passage through the device the host fluid is returned to the host.) The device includes a source of a therapeutic substance, e.g., an islet, and a capture agent, e.g., an antibody which binds antigens or epitopes other than the therapeutic substance released by the source. The source is separated from the host body fluid by a semipermeable component. Preferably a semi-permeable component also separates the capture agent, from the host body fluid. The capture agents should be in a different compartment than the source of a therapeutic substance, or otherwise immobilized to keep it from contacting the source of a therapeutic substance. The capture agent can, e.g., be coupled to the surface of the microreactor, or to the surface of a component of the microreactor.

In preferred embodiments, the capture agent is an antibody or antibody fragment, even more preferably, the capture agent is an antibody or antibody fragment which binds an antigen or epitope other than the therapeutic substance released by the source. In an even more preferred embodiment, the antibody or antibody fragment is directed against an antigen which is an MHC class I, an MHC class II, an SLA class I, or an SLA class II antigen. In another preferred embodiment, the antibody or antibody fragment is a human antibody, a humanized antibody, an antibody which is engineered to minimize host response, or an engineered binding protein of a parental protein which is preferably of human origin.

In preferred embodiments, the device includes a cell or tissue. The cell or tissue can be autologous, allogeneic, or xenogeneic, with regard to the subject. A xenogeneic cell or tissue can be from a species which is concordant or discordant with the subject. The cell or tissue can be from the subject, but if it is from the subject, it is preferably genetically engineered to express a substance not normally expressed by or on that cell or tissue.

In preferred embodiments, the cell or tissue is from a a dog, pig, goat, rabbit, horse, cow, or sheep, or a non-human primate species.

In preferred embodiments, the cell is a pancreatic islet cell. In preferred embodiments, the pancreatic islet is from a dog, pig, goat, rabbit, horse, cow, sheep, or a non-human primate. In particularly preferred embodiments, the pancreatic islet is from a pig. In preferred embodiments, the pancreatic islet is from a human other than the subject.

In preferred embodiments, the cell or tissue is genetically engineered.

The cell or tissue can be from the pancreas, adrenal gland, brain, kidney, liver, thymus parathyroid or thyroid. In a preferred embodiment, the cell is a cultured cell. In a preferred embodiment, the cell is from a primary culture. In a preferred embodiment, the cell has been treated with a cytokine or a growth factor.

In preferred embodiments: the cell is an immortalized cell; the cell is a blood cell; the cell or tissue is a fetal; the cell is a skin, astroglial, or myoblast cell.

In preferred embodiments the device includes a port for admitting flow of the body fluid into the device which port communicates with a chamber which encloses a source of a therapeutic substance, e.g., an islet, and a capture agent, e.g., an antibody which binds antigens or epitopes other than the therapeutic substance released by the source. The source is separated from the host fluid by a semipermeable component, and preferably, the capture agent is separated from the source by a semipermeable component. The fluid exits the device by the same port or by a second port. The device can be used in "batch" or continuous flow fashion.

In preferred embodiments the semipermeable component includes the three-part composite layer described herein.

The methods of the invention allow implanting of allogeneic or xenogeneic tissue with little or no immunosuppression.

Unless otherwise defined, all technical and scientific terms used herein have the same meaning as commonly understood by one of ordinary skill in the art to which this invention belongs. Although methods and materials similar or equivalent to those herein can be used in the practice or testing of the present invention, the preferred methods and materials are described below. All publications, patent applications, patents, and other references mentioned herein are incorporated by reference. In addition, the materials, methods, and examples are illustrative only and not intended to be limiting.

Other features and advantages of the invention will be apparent from the following detailed description and from the claims.

DETAILED DESCRIPTION

CAPTURE AGENTS

Figure 1:
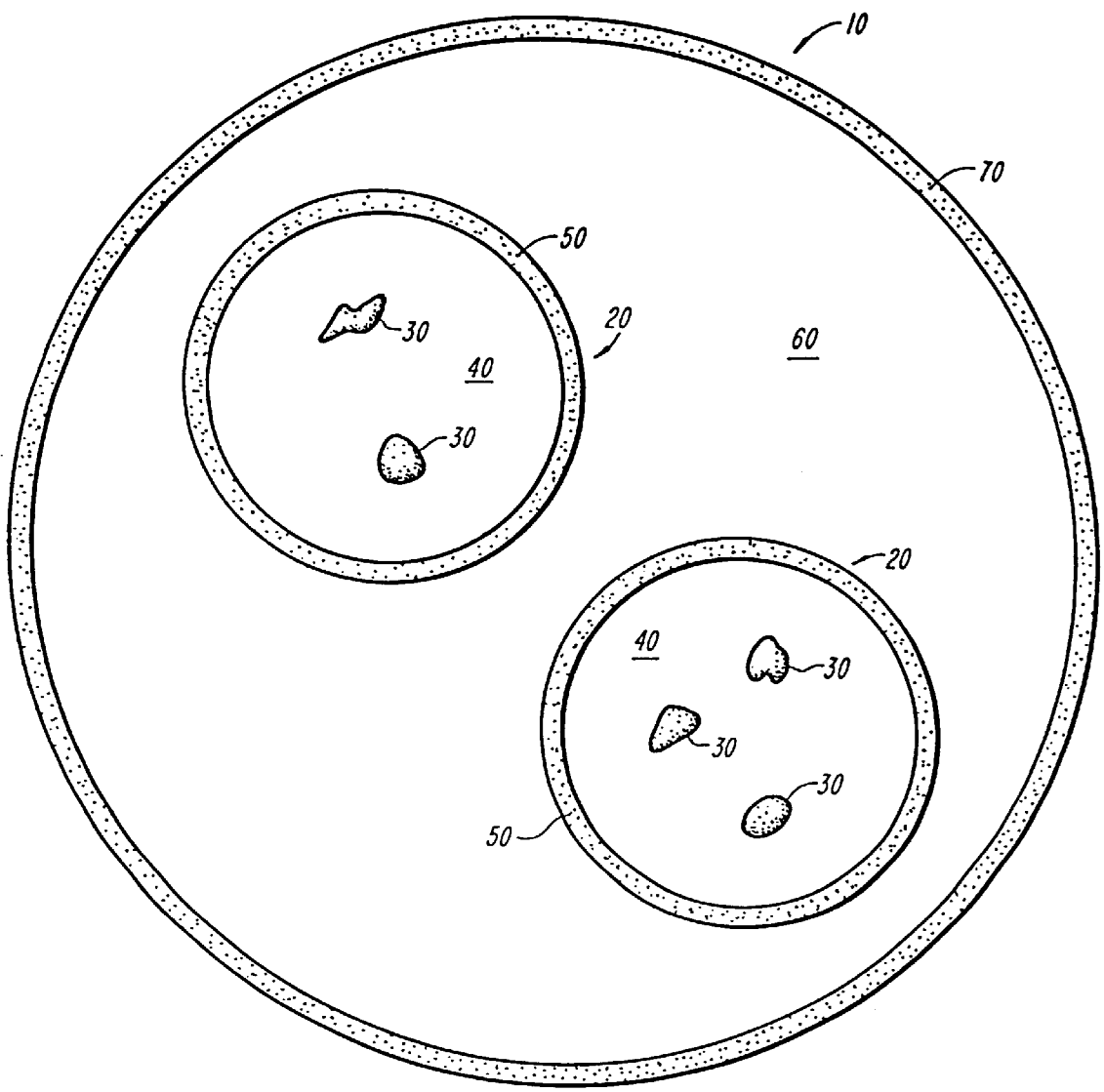
FIG. 1 is a schematic diagram of a composite microreactor.

Capture agents are molecules which inhibit (e.g., reduce or prevent) the release from an implantable device of non-therapeutic, therapeutic source-derived substances capable of stimulating an immune response against the therapeutic source or the device, in a recipient host. A non-therapeutic substance or component, as used herein, refers to molecules, e.g., proteins and peptides, secreted or released from the therapeutic source which are different from the therapeutic substance. For example, non-therapeutic components include decomposition products which may trigger an immune response by the recipient host if the products are released from the implantable device. In the case where the source of a therapeutic substance is swine islet cells and the therapeutic substance is insulin, the capture agent can inhibit the release of islet decomposition products, but does not inhibit the release of insulin.

Capture agents include molecules, e.g., peptides, which have reactivity with a component, other than a therapeutic substance, which is secreted or released from the source. The capture agent can act by binding, sequestering, or otherwise inhibiting the release of non-therapeutic substances, e.g., decomposition products, from the implantable device.

The capture agent can be an antibody which binds to a non-therapeutic substance thereby reducing or preventing release of the non-therapeutic substance from the implantable device. The antibody capture agent can be directed against, for example, an antigen present on the therapeutic source which is capable of stimulating an immune response in an allogeneic or xenogeneic host upon release of the antigen from the device. Examples of such antigens include MHC class I and class II antigens, e.g., in the case of a porcine source, SLA class I or class II antigens. Other antigens include carbohydrate epitopes, e.g., α-galactose epitopes, which are secreted or released from a source and are capable of stimulating an immune response in an allogeneic or xenogeneic host.

A capture agent can be species specific such that the capture agent specifically reacts with a non-therapeutic component of the mammal from which the therapeutic source is obtained. Examples of mammals which the capture agent can be reactive with include pig, dog, goat, rabbit, horse, cow, sheep or non-human primates. In a preferred embodiment, the capture agent specifically reacts with a non-therapeutic component released or secreted from a porcine source. For example, an antibody capture agent can bind an antigen present on the surface of a porcine source, e.g., SLA class I or class II antigen or α-galactose epitope, which is capable of stimulating an immune response in the recipient host if the antigen is released from the implantable device.

The capture agent can be an antibody, or fragment, or derivative thereof which retains the ability to bind to a non-therapeutic substance secreted or released from the source. An antibody, or fragment or derivative thereof, can be derived from polyclonal antisera reactive with a number of epitopes of a source antigen. The antibody can also be a monoclonal antibody directed against the antigen. Antibody fragments and derivatives include, for example, Fv fragments, F(ab) fragments, F(ab')$_2$ fragments, chimeric and humanized antibody. Antibodies can be fragmented using conventional techniques such as enzyme treatment, e.g., pepsin treatment.

Polyclonal and monoclonal antibody capture agents can be prepared by standard techniques known in the art. For example, a mammal, (e.g., a mouse, rabbit, goat or dog) can be immunized with the antigen or with a cell which expresses the antigen (e.g., on the cell surface) to elicit an antibody response against the antigen in the mammal. Alternatively, tissue or a whole organ which expresses the antigen can be used to elicit antibodies. The progress of immunization can be monitored by detection of antibody titers in plasma or serum. Standard ELISA or other immunoassay can be used with the antigen to assess the levels of antibodies. Following immunization, antisera can be obtained and, if desired, polyclonal antibodies isolated from the sera. A monoclonal antibody can be prepared and isolated using a hybridoma technique which provides for the production of antibody molecules by continuous cell lines in culture. Hybridoma cells can be screened immunochemically for production of antibodies specifically reactive with the antigen and monoclonal antibodies isolated.

An antibody capture agent can be derived from the same species as the recipient or host or an antibody which is engineered to minimize host response to the antibody, thereby inhibiting the host's immune system from recognizing a capture agent antibody released from the implantable device, or a capture agent antibody immobilized to the outer surface of the device. For example, if the recipient host of the implantable device is a dog, the antibody capture agent can be prepared by immunizing a dog with a protein derived from an allogeneic or xenogeneic donor source.

In a preferred embodiment, the antibody capture agent is one which is selected to minimize its recognition as foreign by a human recipient. One method of obtaining such antibody capture agents is to engineer a recombinant chimeric or humanized antibody derived from a non-human antibody. Alternatively, a human monoclonal antibody capture agent or fragment directed against an allogeneic or xenogeneic protein can be produced using transgenic mice which express human immunoglobin genes, SCID-hu mice, Rag-1 deficient mice or Rag-2 deficient mice (available from Taconic Farms, Germantown, N.Y.). In addition, human monoclonal antibodies, fragments and single chain antibodies can be expressed in bacteria using phage display expression to create a combinatorial library which is screened for binding affinity to a non-therapeutic, source-derived substance.

The capture agent can also be a an engineered binding protein, e.g., a ligand, or peptide which retains the ability to bind to a non-therapeutic component released or secreted from a therapeutic source. Such a peptide capture agent can be, for example, a soluble form of a receptor for a non-therapeutic substance. In one case, the peptide capture agent can mimic a region of T cell receptor which contacts and binds MHC class I or class II antigens.

A soluble form of a ligand can be made by standard recombinant DNA procedures, using a recombinant expression vector containing DNA encoding the ligand encompassing an extracellular domain (i.e., lacking DNA encoding the transmembrane and cytoplasmic domains). The recombinant expression vector encoding the extracellular domain of the ligand can be introduced into host cells to produce a soluble ligand, which can then be isolated. In addition, protein or peptide capture agents with greater binding affinity for a non-therapeutic substance can be obtained by mutating a protein to create a recombinant combinatorial library and then screening the library for proteins or peptides which bind to the non-therapeutic component. Moreover, protein or peptide capture agents which bind to a non-therapeutic source can also be obtained by screening existing libraries for molecules which bind to a non-therapeutic antigen from the source.

Lectins and selectins can also be used as capture agents which bind to a non-therapeutic source-derived substance, e.g., a carbohydrate molecule or glycoprotein, which is released or secreted from the therapeutic source and which is believed capable of stimulating an immune response in an allogeneic or xenogeneic host recipient. For example, in the case where the source is porcine islet cells and the host recipient is a human, a lectin capture agent which binds to a non-therapeutic carbohydrate molecule, such as a α-galactose epitope, can be used to inhibit the release of a carbohydrate molecule from the implantable device. Preferably, the molecular weight of a lectin or selectin capture agent is higher than the porosity of the microreactor such that passage of the capture agent from the device is hindered. Examples of lectin capture agents include *Datura stramonium, Triticum vulgaris, Sambucus nigra, Bandeiraea simplicifolia, Macluna pomifera* and *Vigna radiata* (all available from Sigma Chemical Corp., St. Louis, Mo.). In addition, selectin capture agents such as leukocyte homing receptor (LAM-1), endothelial leukocyte adhesion molecule (ELAM-1) or CD62 can be used.

Determination of Capture Agent Suitability

An assay for implantable device glucose response can be used to determine effectiveness of a capture agent. Porcine islet implantable devices which include the capture agent are implanted in a suitable host, for example, a dog. Control implantable devices without the capture agent are implanted in a similar host dog. After being implanted for a length of time sufficient for the host molecules to attack the implanted tissue, the implantable devices are removed from the host and cultured in vitro for assay of glucose response to measure islet function, and/or for standard histological staining to analyze viability, e.g., with hematoxylin and eosin. Devices with the suitable capture agent can contain a larger number of viable-staining cells than the control devices. Viable cells are seen as having pink cytoplasm and a blue nucleus. Non-nucleated cells are non-viable. Alternatively, the use of supervital dyes, acridine orange and propidium iodide, yields viable cells stained green, and dead cells stained red.

Further, functional islet-containing implantable devices should alter secretion of insulin in response to altered glucose concentration. For example, a shift of glucose level in the medium in which devices are incubated in vitro from basal level (50 mg/dl glucose) to a stimulatory level (300 mg/dl) should induce a three-to six-fold increase in insulin secretion in vitro which can be sustained for one hour. Further, insulin secretion should return to basal levels after perfusion of implantable devices with basal glucose solution. A suitable capture agent can thus be identified as an agent that, when included in one or more compartments of the implantable devices, maintains ability of both cell viability and the devices to respond to altered glucose concentration, in comparison to the control devices in the absence of the suitable capture agent. Finally, the microreactors containing a capture agent, and control microreactors, can be implanted into diabetic mice. The ability of the microreactor implant to sustain the diabetic rat and replace insulin therapy is determined for the devices with and without the capture agent.

Implantable Devices

An implantable device typically includes a matrix, e.g., gel, e.g., a hydrogel, or core in which living cells are disposed and optionally a semipermeable coating enclosing the gel. The capture agent can be disposed within the gel core or adhered to one or more coatings. If disposed within the gel core, it should be sequestered from the cells and should cloak the cells from cytotoxic antibodies of the host, e.g., by permselective coating, e.g., PLL or PLO. The coating often has a porosity which prevents components of the implant recipient's immune system from entering and destroying the cells within the implantable device. Many methods for encapsulating cells are known in the art. A few are cited below. These are cited merely as examples, and are not the only methods which can be used with the invention.

Encapsulation using a water soluble gum to obtain a semi-permeable water insoluble gel to encapsulate cells for production and other methods of encapsulation are disclosed in U.S. Pat. No. 4,352,883 issued Oct. 5, 1992.

U.S. Pat. No. 4,409,331 issued Oct. 11, 1983 discloses a process for production of substances from encapsulated cells, molecular weight cut-off of membranes, use of divalent cations for polymerization, use of various therapeutic substances, core materials, and methods of formation of the gel including cross-linkers.

Shape-retaining gelled masses that expand before membrane formation, and upon contact with chelator can be made to liquefy within the membrane, and having an optional second membrane are disclosed in U.S. Pat. No. 4,663,286 which issued May 5, 1987.

Double-membrane capsules with high molecular weight cut-offs such as 200–400 kD for the inner membrane, enabling higher density growth of encapsulated cells, and use of poly-L-lys, are disclosed in EPO Publ. No. 0301 777 of Jan. 2, 1989.

U.S. Pat. No. 5,084,350 issued Jan. 28, 1992, discloses gels reliquified within the capsule for a variety of biological samples, and materials for other implantable device components.

U.S. Pat. No. 5,427,935 issued Jun. 27, 1995, discloses composite hybrid membranes of compositions that include chitosan.

Implantable devices with multiple coatings including a halo layer, and not requiring a poly-L-lysine or other polyamino acid or polycation coating are disclosed in WO 95/19743 published Jul. 27, 1995.

Macrocapsular surfaces of decreased surface area and roughness and increased cryoprotectivity, with a variety of co-monomers and free radical initiators of polymerization, are disclosed in U.S. Pat. No. 5,545,423 which issued Aug. 13, 1996

Methods of the invention can be used with any implantable device which is suitable for delivery and maintenance of biologically active material. Such devices include gel-based implantable devices, for example, the composite implantable devices described herein and in U.S. Pat. No. 5,427,935 (Jun. 27, 1995). However, other devices can be used as well, for example, the devices described in U.S. Pat. No. 4,663,286 (May 5, 1987), particularly, the implantable devices described in U.S. Pat. No. 5,545,423 (Aug.13, 1996).

Sources of Therapeutic Substances

Implantable devices used in methods of the invention will generally include a source of a therapeutic substance, e.g., a cell or tissue. The source should release a therapeutic substance which is different from the antigens for which the capture agent has specific affinity.

Preferably the source will be one or more living cells. Cells can be growth-inhibited, such that they do not divide, but continue to perform metabolic reactions. Growth inhibition can be achieved by one or more methods known to one with skill in the art, such as irradiation with UV light, by treatment with mitomycin, and by appropriate genetic manipulation. Exemplary cells include pancreatic islets, hepatic cells, neural cells, liver cells, renal cortex cells, vascular endothelial cells, thyroid and parathyroid cells, thymic cells, ovarian cells, blood cells, allografts or xenografts, and genetically engineered cells. Sources of cells and tissues containing cells include, without limitation, tissue or cells removed from a donor animal, tissue or cells of a primary cell culture obtained by incubation or cultivation of donor tissues and cells, cells obtained from viable cell lines and immortalized cell lines, biologically active products of cells or tissues, and the like. Cells from a primary cell line can be treated in culture with one or more cytokines or growth factors. Exemplary cells for transplantation into a subject can be from the same species as that subject, or from a different species that is discordant or concordant with the recipient subject.

In preferred embodiments the cell is an autologous cell, an allogeneic cell, or a xenogeneic cell. For example, the cell is: an autologous cell, i.e., a cell which is taken from the individual recipient into which the cell will be implanted; an allogeneic cell, i.e., a cell which is taken from a different individual of the same species as the recipient into which the cell will be implanted; a xenogeneic cell, i.e., a cell which is from a different species than the recipient into which the cell will be implanted. In the case of an allogeneic cell, the cell can be fully matched or partially matched for MHC class I loci, fully matched or partially matched for MHC class II loci, and fully matched or partially matched for minor loci. In the case of xenogeneic cells, the cells can be concordant or discordant with respect to the recipient.

In preferred embodiments the recipient animal is a dog, a pig, or a human. In preferred embodiments the donor cell is a pancreatic islet cell. In preferred embodiments: the composite implantable device contains pancreatic islets, e.g., at e.g., a density of 5,000 to 100,000 islets per milliliter of medium; the composite implantable device contains living cells at a density of about $10^4$ to $10^8$ cells per milliliter of medium.

Implantable devices used in the methods described herein can include a source of a therapeutic substance. For example, the device can include, a composition of matter which produces or releases a therapeutic substance, e.g., a protein, e.g., an enzyme, hormone, antibody, or cytokine, a sense or anti-sense nucleic acid, e.g., DNA or RNA, or other substance which can exert a desired effect on a recipient. The source of a therapeutic substance can be a tissue or a living cell; a eukaryotic cell, e.g., a rodent, canine, porcine, or human cell; a prokaryotic cell, e.g., a bacterial cell; a fungal or plant cell; a cell which is genetically engineered, e.g., a cell which is genetically engineered to produce a protein, e.g., a human protein. The source of a therapeutic substance can be or include an autologous, an allogeneic, or a xenogeneic cell. For example, the cell is: an autologous cell, i.e., a cell which is taken from the individual recipient into which the cell will be implanted; an allogeneic cell, i.e., a cell which is taken from a different individual of the same species as the recipient into which the cell will be implanted; a xenogeneic cell, i.e., a cell which is from a different species than the recipient into which the cell will be implanted. In the case of an allogeneic cell, the cell can be fully matched or partially matched for MHC class I loci, fully matched or partially matched for MHC class II loci, and fully matched or partially matched for minor loci. In this case of xenogeneic cells, the cells can be concordant or discordant with respect to the recipient.

Implantable devices used in the methods described herein can include a composition of matter which absorbs or modifies or detoxifies a substance produced by the recipient.

Genetically modified cells can be used. This includes cells that have been modified by genetic engineering to produce a product, e.g., cells modified to overproduce a product they normally produce, as well as cells engineered to produce a produce they do not normally make. Cells which have been modified in other ways, e.g., cells modified to reduce an immune response in a subject e.g., cells modified so as not to produce an antigen other than the therapeutic substance, can also be used in methods of the invention.

Isolation of Cells

Living cells can be isolated away from surrounding tissues or grown in culture by procedures known to the art, and then suspended in a liquid medium prior to encapsulation. The living cells can provide biological substances, e.g., enzymes or co-factors, hormones, clotting factors, or growth factors. Cells, e.g., pancreatic cells, can provide enzymatic or hormonal functions. Cells such as hepatic cells can provide a detoxification function.

As an example, pancreatic islet cells were prepared from either adult mongrel dogs, pigs, or bovine calves (0–2 weeks old) by a modification of the methods of Warnock and Rajotte, *Diabetes,* 37:467 (1988), as previously described in Lanza et al., *Proc. Natl. Acad. Sci.,* 88:11100–11104 (1991).

Briefly, aseptic, viable porcine pancreata were obtained under aseptic operating room procedures. After resection (warm ischemia for less than about 15 minutes), the glands were cannulated and infused with cold (4° C.) University of Wisconsin (UW) organ preservation solution. Pancreatic tissues were dissociated using an intraductal collagenase digestion procedure. The collagenase is delivered by peristaltic pump, and the digested pancreas is mechanically disrupted in a polypropylene dissociation chamber containing 2–6 mm glass beads. The islets were separated from the exocrine tissue by discontinuous density gradient centrifugation (27%, 20.5%, and 11% (w/v) FICOLL® (Sigma, F 9378) in Eurocollins solution).

Isolated islets were then cultured for one day either in M199/Earle's medium supplemented with 10% (vol/vol) fetal bovine serum, 30 mM HEPES, 100 milligrams/dl glucose, and 400 IU/ml penicillin (canine), or in α-MEM plus 10% heat-inactivated horse serum (bovine and porcine) in a humidified atmosphere of 5% $CO_2$/95% air at 37° C. A typical yield of islets should be in the range of $0.05 \times 10^6$, to $0.1 \times 10$, to $0.5 \times 10^6$, to $1.0 \times 10^6$, to $1.8 \times 10^6$ islets for adult pancreas (400 gm wet weight, islet diameter 80–125 µm, purity 85–95%, viability greater than 90%; see below). The cells can also be isolated by other procedures and cultured under other suitable conditions.

Ischemic deterioration of the islet cells is minimized by using tissue fragments of a suitable size, e.g., islet fragments should be less than about 150 microns, and preferably 50 to 125 microns, in diameter. Viability, growth, longevity, and/or function of the islet cells can be enhanced by co-culturing, i.e., by mixing other cell types in the liquid medium prior to encapsulation. Useful cell types include cells which secrete growth hormone, e.g., GH-3 cells, or cells which secrete connective tissue and/or extracellular matrix components, e.g., fibroblasts and endothelial cells. In addition, cells, e.g., islets, can be co-cultured with red blood cells, or hemoglobin, or other oxygen carrying agents can be added, to enhance oxygen availability. Red blood cells can also be used to rescue tissue from damaging effects of nitric oxide.

Islet quality control procedures are used to enable comparison of different lots of islets prepared at different times. Purity (amount of islet tissue compared to exocrine tissue contamination) can be determined by ability of pancreatic islets to rapidly take up diphenyl thiocarbazone (dithizone). Islets can be incubated for five to ten minutes with 50 micrograms/ml of dithizone (D5130, Sigma) to stain them red. The preparation is then examined under light microscopy for a qualitative estimate of purity. Quantification of purity is effected by islet dispersion and counting of stained and unstained cells, or with a spectrophotometric assay of dithizone uptake/micrograms DNA.

Viability can be determined by any one of several assays that depend on the capability of viable cells to exclude certain dyes. For example, one assay uses a combination of the fluorescent stains acridine orange, which stains only viable cells green, and propidium iodide, which stains only the nuclei of dead cells red. The islets are incubated with the dyes (acridine orange, Sigma A6014, 50 micrograms/ml, and propidium iodide, Sigma P4170, 2.5 micrograms/ml) in a PBS solution for 10 to 15 minutes and then dispersed into single cells. Counts of red and green fluorescing cells are used to calculate percent viability.

Insulin secretory activity of the islets is determined both in static culture, e.g., expressed as units of insulin per islet volume, and based on the capability of the islets to respond to graded concentrations of glucose. These values are quantitatively established by measuring the insulin secreted by islets exposed to a range of glucose concentrations extending from 2.8 to 28 milliM glucose.

Formation of Implantable Devices

Living cells, e.g., islet cells, can be encapsulated in a variety of gels, e.g., alginate, to form implantable devices, e.g., microparticles, e.g., microbeads or microspheres to physically isolate the cells once implanted into a host. To prevent entry of smaller molecular weight substances such as antibodies and complement (with a molecular weight of about 150 kDa) into these microparticles, they can be coated with a material such as poly-L-lysine, chitosan, or PAN-PVC, which provides an outer shell with a controlled pore size, or they can be treated by, e.g., cross-linking, to control their internal porosity. Alternatively, their porosity can be controlled by mixing various substances such as polyethylene oxide (PEO) directly into the gel mixture. The use of a high molecular weight molecule, e.g., a high molecular weight PEO, e.g., of about 1–8 million Da, will minimize the escape of the porosity controlling substance. Molecules of this size range can be used with or without an outer coating.

Encapsulation

The description below is directed to primarily to the formation of microcapsules, but the cells can also be incorporated into other implantable devices, e.g., implantable macroencapsulation-devices, perfusion based devices such as "hockey puck" type devices and extra corporeal devices.

Once the cells are isolated and suspended in liquid medium, they can be encapsulated by a supporting matrix, e.g., a hydrogel matrix to form a microbead, which serves as a core of an implantable device, e.g., or internal particle. The core maintains a proper cell distribution, provides strength, and enhances cell viability, longevity, and function. The core can also contribute to immnunoisolation. For example, the physical distance that is created by embedding the internal particle in a supporting matrix, can provide protection from, e.g., nitric oxide and cytokines. It also protects the internal particle from direct cell-cell interactions that can elicit an undesirable host response.

Using standard techniques, a gel matrix is formed by adding cells, e.g., pancreatic islets, to a solution of nutrient medium and liquefied gel, e.g., sodium alginate, to form a suspension, and then crosslinking the gel. A capture agent can be added at this stage. The gel matrix can be any one or a combination of a variety of substances, preferably substances that are biocompatible with the host animal, and are capable of maintaining cellular viability and physically supporting the tissue or cells in suspension.

The gels can be gelled or crosslinked, e.g., by the addition of ions such as calcium, potassium, or barium, or by a change in temperature. If temperature change is used, however, care should be taken to choose appropriate temperature changes for gelation that are not harmful or fatal to the living cells to be encapsulated. Temperature-independent gels include alginates, carrageenans, and gums such as xanthan gum. As used herein, the term alginate includes alginate derivatives. These gels should be treated using standard techniques, to remove polyphenols, lipopolysaccharides, endotoxins, and other impurities.

Alginate is composed of blocks of 1,4 linked β-D-mannuronic acid (M) and α-1-guluronic acid (G) linked together, e.g., in alternating MG blocks. The preferred alginate is one formulated with a high G block content, e.g., at least about 60 percent. The higher the percentage of G blocks in the alginate composition, the greater the pore size and the strength of the gel matrix that is obtained in the final product. In addition, alginate gels with a high M block content appear to be more immunogenic than gels with a high G block content. See, e.g., Soon-Shiong et al., *Transplant. Proc.*, 23:758–759 (1991), and Soon-Shiong et al., *Transplantation*, 54:769–774 (1992).

The gel matrix should be sufficiently viscous to maintain the cells in a dispersed state. When alginate is used as the gel matrix, it is added up to about 3%, preferably to about 1 to 2%, of the liquid medium, and the solution is cross-linked to form a semisolid gel in which the cells are suspended. These percentages provide a matrix that maintains its shape and has sufficient mechanical strength to remain intact in vivo for several months.

Alginate hydrogels are preferred for the microbead cores for a number of reasons. Alginate allows rapid polymerization and immobilization of cells at room temperature using relatively benign $CaCl_2$, provides consistent gel rheology that can be conveniently varied by increasing alginate concentration, and produces microbeads with good mechanical strength.

A preferred method for making hydrogel microbeads is with an air jet.

Other methods for making hydrogel microbeads including emulsification, use of an electrosprayer, dripping, and the Rayleigh jet.

Controlling Pore Size of Microparticles

The pore size of the microparticles can be controlled either by applying a semipermeable shell having a particular molecular weight cutoff. This can be effected by applying an "electrostatic" coating, e.g., a coating of a polyamino acid, e.g., polylysine. Pore size can also be controlled by treating the gel matrix of the microparticles themselves to change the pore size of the matrix without any subsequent coating. E.g., the surface of the core can be altered by, e.g., cross-linking, to produce covalently modified gel matrix surface. A coating can be a formed by modifying the structure of the matrix, e.g., the matrix can be cross-linked, e.g., with metal ions, e.g., Ba or Fe ions, or by photo-cross-linking, to form an coating.

As used herein, "molecular weight cutoff" refers to the size of the largest molecule that is not substantially blocked, e.g., by a semipermeable shell or coating surrounding a microsphere or by the gel matrix itself or both. Molecules with a molecular weight above the cutoff are substantially prevented from entering or leaving the particle. The composite implantable device should generally provide a molecular weight cutoff of about 50 kDa, more preferably about 100 kDa, more preferably about 150 kDa, and most preferably about 400,000 daltons. In preferred embodiments, the molecular weight cutoff is sufficient to prevent Ig molecules, e.g., IgG, and complement, from entering and coming into contact with the encapsulated material.

Altering the Pore Size of the Gel Matrix

The pore size of the gel matrix can be altered in several ways. For example, the gel matrix can be altered, e.g., the porosity can be either increased or decreased so as to influence the transport properties, e.g., permeability and/or molecular weight cutoff, by adding, e.g., gelatin, or collagen, or barium, or other ions with the same valance as $Ca^{++}$ ions. Changes in the temperature will also affect the pore size. An increase in the temperature will result in shrinkage of the gel matrix. The addition of compound, e.g., PEO or PEG, to the gel matrix can also result in altered pore size. PEO or PEG can act to repel protein and to hinder fibrotic response. In preferred embodiments, PEO of molecular weight greater than 1,000 kDa, more preferably greater than 4,000 kDa, and most preferably greater than 8,000 kDa, is mixed with the gel matrix. PEO of relatively high molecular weight will not diffuse out and thus does not require crosslinking.

Coating with Polylysine

To coat an alginate core with polylysine the alginate core is dropped into a solution of 0.05% polylysine in serum free culture medium. The thickness of the polylysine coating can be increased by increasing the time the alginate core is left in the solution, or alternatively, by increasing the concentration of the solution. The volume of beads to solution can be, e.g., 1:5, 1:10, or 1:20. For smaller beads a greater proportion of solution is desirable.

Coatings Which Minimize Particle Volume

Embodiments of the invention use coatings which reduce the volume of a component, e.g., a core, to which they are applied. For example, a polyamino acid coating, e.g., a polylysine, or polyornithine made from a polyamino acid of a relatively low molecular weight, can result in a significant reduction in the volume of a gel core, e.g., an alginate core, to which it is applied. In many cases the reduction in volume is as much as about 50%, or even 60–70%, or more.

Relatively low molecular weight, as used herein, means about 30,000 Da or less, more preferably about 15 kDa or less, more preferably about 10 kDa or less, more preferably about 8 kDa or less, more preferably about 7 kDa or less, more preferably about 5 kDa or less, more preferably about 4 kDa or less, more preferably about 3 kDa or less, and most preferably about 1.5 kDa or less.

For example, the use of polylysine of a relatively low molecular weight, e.g., 3, 7, or 9.6 kDa, can result in a significant reduction, (approximately 30% in some cases) in the diameter, of the core to which it is applied. In addition to the decrease in volume, the use of a low molecular weight polyamino acid will result in a coat having superior permselective properties. However, the use of a low molecular weight polyamino acid often results in a surface which is "pruned", i.e., relatively convoluted or rough, and which can elicit a fibrotic response. The composite implantable device of the invention, by using this coating on the internal particle, and a smooth surface, e.g., of alginate, on the exterior of the composite implantable device, can obtain the benefits of a coating of relatively low molecular weight and also inhibit fibrosis.

The permselectivity properties of a poly amino acid, e.g., a polylysine, coating improve after the coating has been aged 2 or more hours. Thus, for best results, particles coated with these coatings should not be implanted in recipients until the coating has aged.

Geometric Stabilization

Some particles or components are not geometrically stable immediately after manufacture, e.g., the particle or component can change size or shape. If internal particles which are incorporated into a composite implantable device change geometry, the components of the composite implantable device, e.g., the super matrix or outer coating, can be damaged and the integrity of the composite implantable device can be compromised. Although not wishing to be bound by theory, the inventors believe that changes in the geometry can damage the super matrix or the outer coating, e.g., by inducing fissures or discontinuities. Damaged particles can allow the fibrotic proliferation of host cells on the inner particles when implanted into a host. Therefore, it is often desirable to geometrically stabilize internal particles, preferably prior to incorporating them into composite implantable devices. Stabilization can generally be accomplished by allowing the particles to "age" for a short time before incorporation into larger structures. The aging should be done under condition which maximizes the viability of encapsulated cells. Geometric stabilization is particularly important when the particles are coated with a relatively low molecular weight poly-amino acid.

Polylysine-coated alginate particles, especially those coated with relatively low molecular weight polylysine, should be geometrically stabilized. The polylysine coated alginate particles should be placed in a culture medium, suitable for the cell being used, and allowed to stabilize overnight. Geometric stabilization methods taught in PCT/US96/03135 and U.S. patent appln Ser. No. 08/402,209, Filed Mar. 10, 1995, can be used with methods and devices of the invention.

Improved Three-part Composite Semipermeable Coatings

The inventors have discovered a particularly efficacious semipermeable coating to be used in devices of the invention, in particular implantable devices, and in particular microreactors.

Accordingly, in another aspect, the invention features, a semipermeable coating which includes a first, or innermost layer of a polyamino acid; an intermediate gel component, which can be a thin discrete layer but more preferably is integrated into one or both of the polyamino acid layers; and a second or outermost layer of a polyamino acid. This coating is referred to herein as a three-part composite layer. Preferably the layers are adjacent to one another in contact and are not spaced apart. In preferred embodiments the polyamino acid layers are within 10, 5 or 1 or 2 $\mu$m of each other and are more preferably in contact with one another.

The molecular weight of the inner layer of polyamino acid should be chosen such that it is lower than the molecular weight of the outer layer of polyamino acid. Preferably, the inner most layer is in the range of 1–5 kd, more preferably 2–4 kd. In preferred embodiments the molecular weight is about 2 or 3.9. (The molecular weight can be determined by as average molecular weight by viscosity or by Lall's method). Generally the inner layer is chosen to optimize permselectivity, e.g., the ability to exclude IgG. Generally, lowering the molecular weight improves selectivity. However, the use of relatively low molecular weights also have disadvantages, e.g., the use of low molecular weight coatings can result in mechanical instability and the induction of faults or fissures in other components of the microreactor, e.g., in the matrix or super matrix of a microreactor. Such fissures or faults can allow the development of fibrotic proliferation on the surface an internal particle or a particle which has induced faults in the surrounding matrix or super matrix. The disadvantages accompanying the use of such low molecular weight coatings can be overcome by adding to additional members or components to the coating, an intermediate alginate member and second, outermost coating of a polyamino acid. The molecular weight of the inner layer of polyamino acid should sufficiently small that without the other two members of the three part layer it would induce faults in a surrounding matrix.

The intermediate member, is a gel, e.g., alginate. It is an electrostatic component which often does not form a discrete layer between the two polyamino acid layers but rather integrates into the two. If a discreet layer is formed it is thin, e.g., it is no more than 10, more preferably no more than 5, or 1 or 2 $\mu$m in thickness. The gel should be such that it can electrostatically saturate the underlying polyamino acid layer and does not exceed the thickness limitations described herein.

The outer layer of polyamino acid has a higher molecular weight than the inner layer. While molecular weight is minimized in the first layer to maximize permselectivity, a higher molecular weight is used in the outer layer to promote mechanical stability and to prevent the induction of fissures or faults in the surrounding gel matrix or supermatrix. In preferred embodiments the molecular weight is between 5 and 15 and more preferably between 5–15, 8–12, and 9–10 kd. In particularly preferred embodiments the molecular weight is about 9 kd. The molecular weight of the outer layer of polyamino acid should be sufficiently large that in combination with the other two elements, faults are not induced in a surrounding matrix.

In preferred embodiments the coating includes an inner layer of polyamino acid, preferably polylysine, of about 2–4 kd; an intermediate gel member, preferably alginate, which integrates into the inner polyamino acid layer; an outer layer of a polyamino acid, preferably, polylysine, of about 8–12 kd.

This three-part composite layer can be used on any of the devices described herein. In preferred embodiments the three-part composite layer coats: an internal particle of a single composite microreactor; an internal particle of a double composite microreactor; a particle of a double composite microreactor; an internal particle and a particle of a double composite microreactor.

Composite Microreactors Which Include Capture Agents

The inventors have discovered that composite microreactors which include capture agents are particularly useful to immunoisolate donor cells. Composite microreactors which include capture agents allow donor cells, e.g., porcine, bovine, canine, or human islet cells to be successfully transplanted into a host animal, e.g., mouse, rat, dog, or human with little or no need for immunosuppressant or anti-fibrotic drugs. Composite microreactors can be made by the methods taught in PCT/US96/03135 and U.S. patent appln Ser. No. 08/402,209, Filed Mar. 10, 1995.

Accordingly, in one aspect, the invention features, a composite microreactor which includes:
 (a) one, or a plurality, of an internal particle which includes:
  (i) a source of a therapeutic substance, e.g., an islet;
  (ii) an internal particle matrix, e.g., a gel core or a solid particle, which contacts the source;
  (iii) (optionally) an internal semipermeable particle coating enclosing the internal particle matrix; and
 (b) a super matrix, e.g., a gel super matrix, in which the internal particle (or particles) is embedded; and
 (c) (optionally) an outer semipermeable coating enclosing the super matrix, the composite microreactor preferably providing a molecular weight cutoff that prevents molecules larger than about 400,000 daltons from coming into contact with the source.

The composite microreactor includes one or more capture agents. The capture agents should be in a different compartment than is the source of a therapeutic substance, or otherwise immobilized to keep it from contacting the source of a therapeutic substance. The capture agent can, e.g., be coupled to a component of the microreactor, e.g., one or more of the PLL coatings that can comprise a surface of the microreactor, or to the surface of a component of the microreactor.

In preferred embodiments, the capture agent is an antibody or antibody fragment, even more preferably, the capture agent is an antibody or antibody fragment which binds an antigen or epitope other than the therapeutic substance released by the source. In an even more preferred embodiment, the antibody or antibody fragment is directed against an antigen which is an MHC class I, an MHC class II, an SLA class I, or an SLA class II antigen. In another preferred embodiment, the antibody or antibody fragment is a human antibody, a humanized antibody, an antibody which is engineered to minimize host response, or an engineered binding protein of a parental protein which is preferably of human origin.

In preferred embodiments, a capture agent, e.g., an antibody which binds antigens or epitopes other than the therapeutic substance released by the source, is disposed within one or more of an internal particle or the super matrix.

In preferred embodiments, one compartment, e.g., an internal particle, can include the source and a second compartment, e.g., a second internal particle, or the super matrix can include a capture agent.

A compartment can include two or more capture agents, e.g., an engineered humanized anti-porcine Fv and a binding protein for a porcine antigen. A capture agent can be included in more than one compartment.

In preferred embodiments capture agent molecules are present in more than one compartment of a composite microreactor and preferably the concentration or number of capture agent molecules is greater in the compartment which is outer most in the microreactor. Thus, capture agent molecules can be present in on the surface of an internal particle and in the surrounding matrix, but the concentration or number is lower on the surface of the internal particle.

In preferred embodiments: an internal particle is coated with the three-part composite layer described herein.

In preferred embodiments the internal particle matrix is or includes: a gel, e.g., a hydrogel, e.g., an alginate or agarose gel; a solid particle, e.g., a glass bead; a particle having pores or interstices. In preferred embodiments the internal particle matrix is other than a liquid. The internal particle matrix can include substances which impede the passage of recipient-derived molecules or cells, e.g., it can include polyethylene oxide (PEO), or polyethylene glycol (PEG), or polystyrene sulfonic acid (PSA). In preferred embodiments, a capture agent is disposed within the internal particle matrix.

In preferred embodiments the internal particle matrix hinders the passage, and preferably essentially completely prevent the passage of: molecules having a molecular weight of more than about 50 kDa, preferably more than about 100 kDa, preferably more than about 150 kDa, and most preferably more than about 400 kDa; or of immune system components such as Ig molecules or complement.

In preferred embodiments the internal particle coating is or includes: a polyaminoacid, e.g., polylysine (PLL) or polyornithine (PLO); a naturally occurring substance, e.g., chitosan; a synthetic polymer e.g., PAN-PVC. A particularly preferred coating is polyamino acid. e.g., polylysine or polyornithine, having a molecular weight of less than 15 kDa, more preferably of less than 10 kDa, more preferably of less than 5 kDa. Particularly preferred are polyamino acids, e.g., polylysines, with a molecular weight of about 1 kDa–4 kDa, about 1 kDa-less than 4 kDa, e.g., 3.7 kDa, or about 5 kDa to less than about 15 kDa, or about 5 kDa to less than about 10 kDa, e.g., 9 kDa–10 kDa, e.g., 9.7 kDa. Also preferred are polyaminoacid, e.g., PLL or PLO, coatings in the range of 1 or 2–10 kD, preferably in the range of 1–2, 1–3, or 1–4 kD. Preferred coatings are volume-reducing coatings.

In preferred embodiments the internal particle coating hinders the passage, and preferably essentially completely prevent the passage of: molecules having a molecular weight of more than about 50 kDa, preferably more than about 100 kDa, preferably more than about 150 kDa, and most preferably more than about 400 kDa; or of immune system components such as Ig molecules or complement; or host-derived cells.

In preferred embodiments the super matrix is or includes: a gel, e.g., a hydrogel, e.g., an alginate or agarose gel. In preferred embodiments the super matrix is other than a liquid. The super matrix can include substances which impede the passage of recipient-derived molecules or cells, e.g., it can include polyethylene oxide (PEO), polystyrene sulfonic acid (PSA), or polyornithine (PLO). A high molecular weight, molecule, e.g., a polymer, e.g., PEO, with a molecular weight of 1–8 million daltons, or more, can be added to the super matrix to confer immunoisolating properties.

In preferred embodiments a capture agent is disposed covalently bound to the outer layer or to a component within the super matrix.

In preferred embodiments the super matrix hinders the passage, and preferably essentially completely prevent the passage of: molecules having a molecular weight of more than about 50 kDa, preferably more than about 100 kDa, preferably more than about 150 kDa, and most preferably more than about 400 kDa; or of immune system components such as Ig molecules or complement; or recipient-derived cells.

In preferred embodiments the super matrix has little or no ability to exclude low molecular weight species, e.g., IgG or complement, with this property being relegated to other components of the microcapsule.

In preferred embodiments the outer coating (which is optional) is or includes: a polyaminoacid, e.g., polylysine (PLL) or polyornithine (PLO); a naturally occurring substance, e.g., chitosan. A particularly preferred coating is polyamino acid, e.g., polylysine or polyornithine, having a molecular weight of less than 15 kDa, more preferably of less than 10 kDa, more preferably of less than 5 kDa. Particularly preferred are polyamino acids, e.g., polylysines, with a molecular weight of about 1 kDa–4 kDa (or about 1 kDa-less than 4 kDa) e.g., 3.7 kDa, or about 5 kDa to less than 15 kDa, or about 5 kDa to less than about 10 kDa, e.g., 9 kDa–10 kDa, e.g., 9.7 kDa. Also preferred are polyaminoacid, e.g., PLL or PLO, coatings in the range of 1 or 2–10 kD, preferably in the range of 1–2, 1–3, or 1–4 kD.

In preferred embodiments the outer coating hinders the passage, and preferably essentially completely prevent the passage of: molecules having a molecular weight of more than about 50 kDa, preferably more than about 100 kDa, preferably more than about 150 kDa, and most preferably more than about 400 kDa; or of immune system components such as Ig molecules or complement; or host-derived cells.

In preferred embodiments the diameter of the internal particle, before application of a volume-reducing coating, is between 50 and 700 microns, more preferably between 100 and 500 microns, more preferably between 200 and 400 microns, and most preferably about 300 microns in diameter. The diameter of the internal particles, after application of a volume-reducing coating, is preferably between 35 and 500 microns, more preferably between 75 and 400 microns, more preferably between 100 and 300 microns, and most preferably about 200 microns in diameter.

In preferred embodiments the diameter of the composite microreactor is between 100 microns and 4 millimeters, between 300 and 1200 microns, between 300 and 1500 microns, between 400 and 1000 microns, or between 400 and 800 microns. More preferably the diameter is about 600 microns.

In preferred embodiments the composite microreactor includes one or a plurality of internal particles, e.g., between 1 and 100, e.g., 1 and 10, internal particles.

In preferred embodiments the composite microreactor is a component of a higher order composite, e.g., a double composite, or a third order composite.

In preferred embodiments one or more components of the composite is geometrically stabilized, as is taught in PCT/US96/03135 and U.S. patent appln Ser. No. 08/402,209, Filed Mar. 10, 1995. For example: the internal particle matrix is geometrically stabilized, e.g., by allowing it to age for between 2 hours and 14 days, e.g., for between 12 hours and 4 or 5 days, prior to coating it; the internal particle is geometrically stabilized, e.g., by allowing it to age for between 2 hours and 14 days, e.g., for between 12 hours and 4 or 5 days prior to embedding it in the super matrix.

In preferred embodiments the internal particle coating has a lower molecular weight exclusion number than does the super matrix, the outer coating (if present), or the combination of the super matrix and the outer coating, e.g., the internal particle coating excludes recipient immune molecules, e.g., IgG or complement, and the super matrix, the outer coating (if present), or the combination of the super matrix and the outer coating, allows immune molecules, e.g., IgG or complement, to pass but excludes the passage of recipient cells.

In preferred embodiments: the outer surface of the composite is biologically compatible, e.g., it is sufficiently smooth that it inhibits fibrotic encapsulation of the composite; the outer surface of the composite is biologically compatible, e.g., it is sufficiently smooth that it inhibit fibrotic encapsulation of the composite but the surface of the internal particle is not biologically compatible, e.g., it is not sufficiently smooth to inhibit fibrotic encapsulation.

In preferred embodiments: at least one of the super matrix and the outer coating prevents contact of fibrotic cells with the internal particle coating.

In preferred embodiments the composite microreactor further includes:

(b) one, or a plurality, of a second internal particle which includes:
 (i) a second source of a therapeutic substance, e.g., an islet or a cell other than and islet;
 (ii) a second internal particle matrix which includes the second source,
 (iii) (optionally) a second internal particle coating enclosing the second internal particle;

In preferred embodiments: super matrix prevents contact of fibrotic cells with the internal particle coating; the super matrix and the outer coating (if present) is free of defects which arise from the inclusion of non-geometrically stabilized components, e.g., non-geometrically stabilized internal particles; at least two, or three, or four, components chosen from the group of the internal particle matrix, the internal particle coating, the super matrix, and the outer coating (if present), provides a molecular weight cutoff that prevents molecules larger than about 150,000 daltons from coming into contact with the sources; the internal particle molecular weight cutoff is provided by a pore structure of the internal particle matrix, and that pore structure results, e.g., from cross-linking of the internal particle gel; the molecular weight cutoff the super matrix is provided by a pore structure of the super matrix.

Preferred embodiments lack an outer coating.

In preferred embodiments the outer surface of the composite microreactor is a gel, e.g., an alginate gel. In more preferred embodiments the outer surface of the composite microreactor is a gel, e.g., an alginate gel, the outer surface of which has been modified, e.g., by cross-linking, to produce a covalently modified gel surface, e.g., to form a coating.

In preferred embodiments the outer component of the composite microreactor, i.e., the component in contact with the recipient, is at least 50, 75, 90, 95, 97, or 98%, water.

In preferred embodiments one or more components of the composite microreactor is of sufficient diameter, or of sufficient thickness, such that it imposes a substantial distance (or separation) between recipient cells, e.g., lymphocytes, macrophages, or NK cells, and the source of a therapeutic substance. In more preferred embodiments the thickness (e.g., the distance between its inner surface and its outer surface) of a component, e.g., a matrix, e.g., a particle matrix or super matrix, is: at least 5, 10, 20, 50, 75, 100, or 200 microns. In more preferred embodiments the distance between recipient cells and the source of a therapeutic substance is: at least 5, 10, 20, 50, 75, 1 00, or 200 microns; sufficient such that exposure of the source of a therapeutic substance to small molecules (e.g., molecules which are not excluded by a component which excludes IgG, e.g., cytokines, nitric oxide (NO), and other toxic moieties) released by recipient cells is substantially reduced (e.g., by diffusion), e.g., reduced at least 10, 20, 50, 75, or 90%; sufficient such that the concentration of small molecules (e.g., molecules which are not excluded by the semipermeable barrier-components of the composite microreactor, e.g., cytokines, NO, and other toxic moieties) released by recipient cells is substantially reduced (e.g., by diffusion), e.g., reduced at least 10, 20, 50, 75, or 90% at the source of a therapeutic substance. In more preferred embodiments: the distance is supplied by one or both of the particle matrix and the super matrix.

In preferred embodiments one or more components of the composite microreactor is of sufficient diameter, or of sufficient thickness, such that it imposes a substantial distance (or separation) between recipient cells, e.g., lymphocytes, macrophages, or NK cells, and one or both of the source of a therapeutic substance or donor antigen (other than the therapeutic substance) released by the source (e.g., donor proteins, which could stimulate a recipient response against donor tissue). In more preferred embodiments the thickness (e.g., the distance between its inner surface and its outer surface) of a component, e.g., a matrix, e.g., a particle matrix or super matrix, is: at least 5, 10, 20, 50, 75, 100, or 200 microns. In more preferred embodiments the distance between recipient cells and the source of a therapeutic substance is: at least 5, 10, 20, 50, 75, 100, or 200 microns; sufficient such that the amount, number, or concentration of a donor antigen, released into the recipient, or contacting recipient cells, is substantially reduced (e.g., by diffusion, or by trapping in or exclusion by the component or components which supply the separation), e.g., reduced by at least 10, 20, 50, 75, or 90%; sufficient such that contact of cells of the recipient with donor antigens, e.g., proteins, which protrude from or extend through the internal particle matrix or internal particle coating, or both, is substantially reduced (e.g., by diffusion, or by trapping in or exclusion by the component or components which supply the separation), e.g., reduced by at least 10, 20, 50, 75, or 90%; sufficient to inhibit acute release of donor antigens. In more preferred embodiments: the distance or separation is supplied by one or both of the particle matrix and the super matrix.

The inventors have discovered that a single or simple composite microreactor, e.g., one which includes one or more microcapsules contained in a larger particle, and which include a capture agent, can be used to immunoisolate donor tissue. They have further discovered that higher order composites, e.g., double composites, which include one or more single composites contained in a larger particle, and which include a capture agent, are also effective for immunoisolating donor tissue.

Accordingly, the invention features, a double composite microreactor which includes:

(1) one, or a plurality, of an internal particle which includes:
 (a) a source of a therapeutic substance, e.g., an islet;
 (b) an internal particle matrix which contacts the source; and
 (c) (optionally) an internal particle semipermeable coating enclosing the first internal particle matrix;

(2) one, or a plurality, of a particle which includes:
 (a) the internal particle or particles of (1)
 (b) a particle matrix in which the internal particle (or internal particles) is embedded; and (c) (optionally) a particle semipermeable coating enclosing the particle;

(3) a super matrix in which the particle (or particles) of (2) is embedded; and (4) (optionally) a super matrix or outer semipermeable coating, e.g., of polylysine enclosing the super matrix.

In preferred embodiments the internal particle matrix is or includes: a gel, e.g., a hydrogel, e.g., an alginate or agarose gel; a solid particle, e.g., a glass bead; a particle having pores or interstices. In preferred embodiments the internal particle matrix is other than a liquid. The internal particle matrix can include substances which impede the passage of recipient-derived molecules or cells, e.g., it can include polyethylene oxide (PEO), polystyrene sulfonic acid (PSA), polyethylene glycol (PEG) or polyornithine (PLO).

The composite microreactor includes one or more capture agents. The capture agents should be in a different compartment than is the source of a therapeutic substance, or otherwise immobilized to keep it from contacting the source of a therapeutic substance. The capture agent can, e.g., be coupled to the surface of the microreactor, or to the surface of a component of the microreactor.

In preferred embodiments, a capture agent, e.g., an antibody which binds an antigen or epitope other than the therapeutic substance released by the source, is disposed within or on the surface of, one or more of an internal particle, a particle, or the super matrix.

In preferred embodiments, the capture agent is an antibody or antibody fragment, even more preferably, the capture agent is an antibody or antibody fragment which binds an antigen or epitope other than the therapeutic substance released by the source. In an even more preferred embodiment, the antibody or antibody fragment is directed against an antigen which is an MHC class I, an MHC class II, an SLA class I, or an SLA class II antigen. In another preferred embodiment, the antibody or antibody fragment is a human antibody, a humanized antibody, an antibody which is engineered to minimize host response, or an engineered binding protein of a parental protein which is preferably of human origin.

In preferred embodiments, one compartment, e.g., an internal particle, can include a first capture agent and a second compartment, e.g., a second internal particle, or a particle matrix, or the super matrix, can include a second capture agent.

A compartment can include two or more capture agents.

A capture agent can be included in more than one compartment.

In preferred embodiments capture agent molecules are present in or on the surface of more than one compartment of a composite microreactor and the concentration or number of capture agent molecules is greater in the compartment which is outer most in the microreactor. Capture agent molecules can be present in two or more of an internal particle, a particle, or the super matrix, and the concentration or number in a compartment which is more inner is less than that in an outer compartment which includes capture agents. In preferred embodiments: capture agent molecules are present on or in an internal particle and a particle and the concentration or number is less in the internal particle; capture agent molecules are present on or in an internal particle and the super matrix and the concentration or number is less in the internal particle; capture agent molecules are present on or in a particle and the super matrix and the concentration or number is less on or in the particle.

In preferred embodiments: an internal particle is coated with the three-part composite layer described herein; a particle is coated with the three-part composite layer described herein; an internal particle and a particle are coated with the three-part composite layer described herein; an internal particle does not include the three-part layer but a particle is coated with the three-part composite layer described herein.

In preferred embodiments cells which produce a therapeutic substance, e.g., islet cells, are disposed in an internal particle and a capture agent, e.g., an antibody, is disposed on the internal particle or in the super matrix.

In preferred embodiments the internal particle matrix hinders the passage, and preferably essentially completely prevents the passage of: molecules having a molecular weight of more than about 50 kDa, preferably more than about 100 kDa, preferably more than about 150 kDa, and most preferably more than about 400 kDa; or of immune system components such as Ig molecules or complement; or host-derived cells.

In preferred embodiments a capture agent is disposed on the surface of the internal particle matrix.

In preferred embodiments the internal particle coating is or includes: a polyamino acid, e.g., polylysine (PLL) or PLO; a naturally occurring substance, e.g., chitosan; a synthetic polymer e.g., PAN-PVC. A particularly preferred coating is polyamino acid. e.g., polylysine or polyornithine, having a molecular weight of less than 15 kDa, more preferably of less than 10 kDa, more preferably of less than 5 kDa. Particularly preferred are polyamino acids, e.g., polylysines, with a molecular weight of about 1 kDa–4 kDa, about 1 kDa-less than 4 kDa. e.g., 3.7 kDa, or about 5 kDa to less than 15 kDa, or about 5 kDa to less than about 10 kDa, e.g., 9 kDa–10 kDa, e.g., 9.7 kDa. Also preferred are polyamino acid, e.g., PLL or PLO, coatings in the range of 1 or 2–10 kD, preferably in the range of 1–2, 1–3, or 1–4 kD. Preferred coatings are volume-reducing coatings.

In preferred embodiments the internal particle coating hinders the passage, and preferably essentially completely prevent the passage of: molecules having a molecular weight of more than about 50 kDa, preferably more than about 100 kDa, preferably more than about 150 kDa, and most preferably more than about 400 kDa; or of immune system components such as Ig molecules or complement; or host-derived cells.

In preferred embodiments the diameter of the internal particle, before application of a volume-reducing coating, between 50 and 700 microns, more preferably between 100 and 500 microns, more preferably between 200 and 400 microns, and most preferably about 300 microns in diameter. The diameter of the internal particles, after application of a volume-reducing coating, is preferably between 35 and 500 microns, more preferably between 75 and 400 microns, more preferably between 100 and 300 microns, and most preferably about 200 microns in diameter.

In preferred embodiments the particle matrix is or includes: a gel, e.g., a hydrogel, e.g., an alginate or agarose gel. In preferred embodiments the particle matrix is other than a liquid. The particle matrix can include substances which impede the passage of recipient-derived molecules or cells, e.g., it can include polyethylene oxide (PEO), polystyrene sulfonic acid (PSA), polyethylene glycol (PEG), or polyornithine (PLO).

In preferred embodiments a capture agent is disposed within the particle matrix.

In preferred embodiments the particle matrix hinders the passage, and preferably essentially completely prevent the passage of: molecules having a molecular weight of more than about 50 kDa, preferably more than about 100 kDa, preferably more than about 150 kDa, and most preferably more than about 400 kDa; or of immune system components such as Ig molecules or complement; or recipient-derived cells.

In preferred embodiments the particle coating is or includes: a polyaminoacid, e.g., polylysine (PLL) or PLO; a naturally occurring substance, e.g., chitosan; a synthetic polymer e.g., PAN-PVC. A particularly preferred coating is polyamino acid. e.g., polylysine or polyornithine, having a molecular weight of less than 15 kDa, more preferably of less than 10 kDa, more preferably of less than 5 kDa. Particularly preferred are polyamino acids, e.g., polylysines, with a molecular weight of about 1 kDa–4 kDa (or about 1 kDa-less than 4 kDa) e.g., 3.7 kDa, or about 5 kDa to less than 15 kDa, or about 5 kDa to less than about 10 kDa, e.g., 9 kDa–10 kDa, e.g., 9.7 kDa. Also preferred are polyaminoacid, e.g., PLL or PLO, coatings in the range of 1 or 2–10 kD, preferably in the range of 1–2, 1–3, or 1–4 kD. Preferred coatings are volume-reducing coatings.

In preferred embodiments the particle coating hinders the passage, and preferably essentially completely prevent the passage of: molecules having a molecular weight of more than about 50 kDa, preferably more than about 100 kDa, preferably more than about 150 kDa, and most preferably more than about 400 kDa; or of immune system components such as Ig molecules or complement; or recipient-derived cells.

In preferred embodiments the diameter of the particle, before application of a volume-reducing coating, is between 200 and 1,000 microns, more preferably between 400 and 800 microns, more preferably between 500 and 700 microns, and most preferably about 600 microns in diameter. The diameter of the particles, after application of a volume-reducing coating, is preferably between 100 and 700 microns, more preferably between 250 and 550 microns, more preferably between 300 and 500 microns, and most preferably about 400 microns in diameter.

In preferred embodiments the super matrix has little or no ability to exclude low molecular weight species, e.g., IgG or complement, with this property being relegated to other components of the microcapsule.

In preferred embodiments a capture agent is disposed on the surface of the super matrix.

In preferred embodiments the gel super matrix is or includes: a hydrogel, e.g., an alginate or agarose gel. In preferred embodiments the super matrix is other than a liquid. The super matrix can include substances which impede the passage of recipient-derived molecules or cells, e.g., it can include polyethylene oxide (PEO), polystyrene sulfonic acid (PSA), polyethylene glycol (PEG), or polyornithine (PLO). A high molecular weight, molecule, e.g., a polymer, e.g., PEO, with a molecular weight of 1–8 million daltons, or more, can be added to the super matrix to confer immunoisolating properties.

In preferred embodiments the super matrix hinders the passage, and preferably essentially completely prevent the passage of: molecules having a molecular weight of more than about 50 kDa, preferably more than about 100 kDa, preferably more than about 150 kDa, and most preferably more than about 400 kDa; or of immune system components such as Ig molecules or complement; or recipient-derived cells.

In preferred embodiments the super matrix has little or no ability to exclude low molecular weight species, e.g., IgG or complement, with this property being relegated to other components of the microcapsule.

In preferred embodiments the super matrix coating (which is optional) is or includes: a polyaminoacid, e.g., polylysine (PLL) or PLO; a naturally occurring substance, e.g., chitosan. Particularly preferred coating is polyamino acid. e.g., polylysine or polyornithine, having a molecular weight of less than 15 kDa, more preferably of less than 10 kDa, more preferably of less than 5 kDa. Particularly preferred are polyamino acids, e.g., polylysines, with a molecular weight of about 1 kDa–4 kDa (or about 1 kDa-less than 4 kDa) e.g., 3.7 kDa, or about 5 kDa to less than 15 kDa, or about 5 kDa to less than about 10 kDa, e.g., 9 kDa–10 kDa, e.g., 9.7 kDa. Also preferred are polyaminoacid, e.g., PLL or PLO, coatings in the range of 1 or 2–10 kD, preferably in the range of 1–2, 1–3, or 1–4 kD.

In preferred embodiments the particle coating hinders the passage, and preferably essentially completely prevent the passage of: molecules having a molecular weight of more than about 50 kDa, preferably more than about 100 kDa, preferably more than about 150 kDa, and most preferably more than about 400 kDa; or of immune system components such as Ig molecules or complement; or recipient-derived cells.

In preferred embodiments the diameter of the double composite microreactor is, before application of a volume-reducing coating, between 400 and 1,500 microns, more preferably between 500 and 1,300 microns, more preferably between 600 and 1,100 microns, and most preferably about 900 microns in diameter. The diameter of the double composite microreactor is, after application of a volume-reducing coating, is preferably between 300 and 1,300 microns, more preferably between 400 and 1,200 microns, more preferably between 500 and 1,000 microns, and most preferably about 800 microns in diameter.

In preferred embodiments the composite microreactor includes a plurality of internal particles, e.g., between 2 and 100, e.g., between 2 and 10, internal particles.

In preferred embodiments the composite microreactor includes a plurality of particles, e.g., between 2 and 100, e.g., 2 and 10, particles.

In preferred embodiments the double composite microreactor is a component of a higher order composite, e.g., a third or fourth order composite.

In preferred embodiment one or more components of the composite is geometrically stabilized, as is taught in PCT/US96/03135 and U.S. patent application Ser. No. 08/402,209, Filed Mar. 10, 1995. For example: the first internal particle matrix is geometrically stabilized, e.g., by allowing it to age for between 2 hours and 14 days, e.g., for between 12 hours and 4 or 5 days, prior to coating it; the first internal particle is geometrically stabilized, e.g., by allowing it to age for between 2 hours and 14 days, e.g., for between 12 hours and 4 or 5 days prior to embedding it in the particle matrix; the first particle matrix is geometrically stabilized, e.g., by allowing it to age for between 2 hours and 14 days, e.g., for between 12 hours and 4 or 5 days, prior to coating it; the first particle is geometrically stabilized, e.g., by allowing it to age for between 2 hours and 14 days, e.g., for between 12 hours and 4 or 5 days prior to embedding it in the super matrix; the super matrix is geometrically stabilized, e.g., by allowing it to age for between 2 hours and 14 days, e.g., for between 12 hours and 4 or 5 days prior to coating it; the coated super matrix is geometrically stabilized, e.g., by allowing it to age for between 2 hours and 14 days, e.g., for between 12 hours and 4 or 5 days.

In preferred embodiments the internal particle coating has a lower molecular weight exclusion number than does the particle matrix, the super matrix, the outer coating (if present), or a combination of one or more of these, e.g., the internal particle coating excludes recipient immune molecules, e.g., IgG or complement, and the particle matrix, super matrix, the outer coating (if present), or a combination of these, allows immune molecules, e.g., IgG, or complement, to pass but excludes the passage of recipient cells.

In preferred embodiments: the outer surface of the composite is biologically compatible, e.g., it is sufficiently smooth that it inhibits fibrotic encapsulation of the composite; the outer surface of the composite is biologically compatible, e.g., it is sufficiently smooth that it inhibit fibrotic encapsulation of the composite but the surface of the internal particle (or of the particle) is not biologically compatible, e.g., it is not sufficiently smooth to inhibit fibrotic encapsulation.

In preferred embodiments: the first source is an islet; the second source is an islet; the third source is an islet; the fourth source is an islet; one source is an islet and another source is other than an islet, e.g. an erythrocyte, an acinar cell, or an adrenal cell.

In preferred embodiments: an internal particle coating is a low molecular weight polyamino acid e.g., 1 kDa–4 kDa, about 1 kDa-less than 4 kDa and a particle coating is a low molecular weight polyamino acid e.g., 5 kDa to less than about 10 kDa, 5 kDa to less than about 15 kDa, e.g., about 9 kDa–10 kDa. Also preferred are polyaminoacid, e.g., PLL or PLO, coatings in the range of 1 or 2–10 kD, preferably in the range of 1–2, 1–3, or 1–4 kD.

In preferred embodiments: an internal particle coating has an exclusion limit of about 150 kDa and the first particle coating has an exclusion limit of about 400 kDa.

In preferred embodiments: an internal particle coating has an exclusion limit of about 150 kDa and the particle matrix, first particle coating, super matrix, outer coating, or a combination thereof, has an exclusion limit of about 400 kDa.

In preferred embodiments: an internal particle coating has an exclusion limit which is lower than that of the particle coating, e.g., the internal particle coating has an exclusion limit which will exclude molecules which are the size of IgG, or Clq, or larger, and the particle coating has an exclusion limit which, though permeable to IgG, or Clq, will exclude objects, e.g., cells, having a molecular weight of one million or more.

In preferred embodiments: an internal particle coating has an exclusion limit which is lower than that of the particle coating, e.g., the internal particle coating has an exclusion limit which will exclude molecules which are the size of IgG, or Clq, or larger, and the particle matrix, first particle coating, super matrix, outer coating, or a combination thereof, has an exclusion limit which, though permeable to IgG, or Clq, will exclude objects, e.g., cells, having a molecular weight of one million or more.

In preferred embodiments: there is a buffer-zone component, e.g., the particle matrix, which is disposed between a component which is not biocompatible, e.g., which is not anti fibrotic, e.g., the internal particle coating, and a component which has an exclusion limit which excludes the passage of recipient cells, e.g., the super matrix or outer coating.

In preferred embodiments: an internal particle coating has an exclusion limit which will exclude molecules which are the size of IgG, or Clq, or larger, the particle matrix is not free of defects which arise from the use of non-geometrically stabilized components, and the super matrix, outer coating, or a combination thereof, has an exclusion limit which, though permeable to IgG, or Clq, will exclude objects, e.g., cells, having a molecular weight of one million or more.

In preferred embodiments, the first particle of the double composite microreactor further includes:
  one, or a plurality, of a second internal particle which includes:
    (i) a second source of a therapeutic substance, e.g., an islet;
    (ii) a second internal particle matrix which contacts the second source;
    (iii) a second internal particle coating enclosing the second internal particle matrix;
In preferred embodiments, the double composite microreactor further includes:
  one, or a plurality, of a second particle which includes:
    (a) a third internal particle which includes:
      (i) a third source of a therapeutic substance, e.g., an islet,
      (ii) a third internal particle matrix which contacts the third source,
      (iii) (optionally) a third internal particle coating enclosing the third internal particle matrix; and
    (b) (optionally) a fourth internal particle which includes:
      (i) a fourth source of a therapeutic substance, e.g., an islet,
      (ii) a fourth internal particle matrix which contacts the fourth source,
      (iii) a fourth internal particle coating enclosing the fourth internal particle matrix.

In preferred embodiments: one or more of the particle matrix, particle covering, or super matrix, prevents contact of host cells capable of fibrotic reactions with the internal particle coating; the particle matrix, super matrix or the outer coating (if present) is free of defects which arise from the inclusion of non-geometrically stabilized components, e.g., non-geometrically stabilized internal particles; at least two, or three, or four, components chosen from the group of the particle matrix, the particle coating, the super matrix, and the outer coating (if present), provides a molecular weight cutoff that prevents molecules larger than about 150,000 daltons from coming into contact with the internal particle coating; the internal particle molecular weight cutoff is provided by a pore structure of the internal particle matrix, and that pore structure results, e.g., from cross-linking of the internal particle gel; the molecular weight cutoff the super matrix is provided by a pore structure of the super matrix.

Preferred embodiments lack an outer coating.

In preferred embodiments the outer surface of the double (or higher order) composite microreactor is a gel, e.g., an alginate gel. In more preferred embodiments the outer surface of the composite microreactor is a gel, e.g., an alginate gel, the outer surface of which has been modified, e.g., by cross-linking, to produce a covalently modified gel surface, e.g., to form a coating.

In preferred embodiments the internal particle coating is polylysine of about 5 kDa to less than about 15 kDa, or about 5 kDa to less than about 10 kDa, e.g., 9 kDa–10 kDa, and the particle coating is polylysine of about 5 kDa to less than about 15 kDa, or about 5 kDa to less than about 10 kDa, e.g., about 9 kDa–10 kDa. Also preferred are polyamino acid, e.g., PLL or PLO, coatings in the range of 1 or 2–10 kD, preferably in the range of 1–2, 1–3, or 1–4 kD.

In preferred embodiments the internal particle coating is polylysine of about 1 kDa–4 kDa (or about 1 kDa-less than 4 kDa) e.g., about 2 kDa–3 kDa, and the particle coating is polylysine of about 5 kDa to less than about 15 kDa, or about 5 kDa to less than about 10 kDa, e.g., about 9 kDa–10 kDa. Also preferred are polyamino acid, e.g., PLL or PLO, coatings in the range of 1 or 2–10 kD, preferably in the range of 1–2, 1–3, or 1–4 kD.

In preferred embodiments the internal particle coating is polylysine of about 1 kDa–4 kDa (or about 1 kDa-less than 4 kDa) e.g., about 2 kDa–3 kDa, and the particle coating is polylysine of about 1 kDa–4 kDa (or about 1 kDa-less than 4 kDa) e.g., about 2 kDa–3 kDa. Also preferred are polyaminoacid, e.g., PLL or PLO, coatings in the range of 1 or 2–10 kD, preferably in the range of 1–2, 1–3, or 1–4 kD.

In preferred embodiments the outer component of the double composite microreactor, i.e., the component in contact with the recipient, is at least 50, 75, 90, 95, 97, or 98%, water.

In preferred embodiments one or more components of the double composite microreactor is of sufficient diameter, or of sufficient thickness, such that it imposes a substantial distance (or separation) between recipient cells, e.g., lymphocytes, macrophages, or NK cells, and the source of a therapeutic substance. In more preferred embodiments the thickness (e.g., the distance between its inner surface and its outer surface) of a component, e.g., a matrix, e.g., a particle matrix or super matrix, is: at least 5, 10, 20, 50, 75, 100, or 200 microns. In more preferred embodiments the distance between recipient cells and the source of a therapeutic substance is: at least 5, 10, 20, 50, 75, 100, or 200 microns; sufficient such that exposure of the source of a therapeutic substance to small molecules (e.g., molecules which are not excluded by a component which excludes IgG, e.g., cytokines, nitric oxide (NO), and other toxic moieties) released by recipient cells is substantially reduced (e.g., by diffusion), e.g., reduced at least 10, 20, 50, 75, or 90%; sufficient such that the concentration of small molecules (e.g., molecules which are not excluded by the semipermeable barrier-components of the double composite microreactor, e.g., cytokines, NO, and other toxic moieties) released by recipient cells is substantially reduced (e.g., by diffusion), e.g., reduced at least 10, 20, 50, 75, or 90% at the source of a therapeutic substance. In more preferred embodiments: the distance is supplied by one or both of the particle matrix and the super matrix.

In preferred embodiments, the distance between the source of the therapeutic substance and recipient [host] cells is sufficient that a capture agent with affinity for antigens found on source cells do not affect the viability of source cells; e.g., antigen release is reduced at least 20%, 50%, 75%, 90%, most preferably 95%, while initial source cell viability remains at least 25%, 70%, 75%, 85%, 95% of initial viability level.

In preferred embodiments one or more components of the double composite microreactor is of sufficient diameter, or of sufficient thickness, such that it imposes a substantial distance (or separation) between recipient cells, e.g., lymphocytes, macrophages, or NK cells, and one or both of the source of a therapeutic substance or donor antigen (other than the therapeutic substance) released by the source (e.g., donor proteins, which could stimulate a recipient response against donor tissue). In more preferred embodiments the thickness (e.g., the distance between its inner surface and its outer surface) of a component, e.g., a matrix, e.g., a particle matrix or super matrix, is: at least 5, 10, 20, 50, 75, 100, or 200 microns. In more preferred embodiments the distance between recipient cells and the source of a therapeutic substance is: at least 5, 10, 20, 50, 75, 100, or 200 microns; sufficient such that the amount, number, or concentration of a donor antigen, released into the recipient, or contacting recipient cells, is substantially reduced (e.g., by diffusion, or by trapping in or exclusion by the component or components which supply the separation), e.g., reduced by at least 10, 20, 50, 75, or 90%; sufficient such that contact of cells of the recipient with donor antigens, e.g., proteins, which protrude from or extend through the internal particle matrix or internal particle coating, or both, is substantially reduced (e.g., by diffusion, or by trapping in with a capture agent or by exclusion by the component or components which supply the separation), e.g., reduced by at least 10, 20, 50, 75, or 90%; sufficient to inhibit acute release of donor antigens. In more preferred embodiments: the distance or separation is supplied by one or both of the particle matrix and the super matrix.

As used herein, a source of a therapeutic substance can include a composition of matter which produces or releases a therapeutic substance, e.g., a protein, e.g., an enzyme, hormone, antibody, or cytokine, a sense or anti-sense nucleic acid, e.g., DNA or RNA, or other substance which can exert a desired effect on a recipient. The therapeutic substance can also be a composition of matter which absorbs or modifies or detoxifies a substance produced by the recipient. The source of a therapeutic substance can be a tissue or a living cell; a eukaryotic cell, e.g., a rodent, canine, porcine, or human cell; a prokaryotic cell, e.g., a bacterial cell; a fungal or plant cell; a cell which is genetically engineered, e.g., a cell which is genetically engineered to produce a protein, e.g., a human protein. The source of a therapeutic substance can be or include an autologous, an allogeneic, or a xenogeneic cell. For example, the cell is: an autologous cell, i.e., a cell which is taken from the individual recipient into which the cell will be implanted; an allogeneic cell, i.e., a cell which is taken from a different individual of the same species as the recipient into which the cell will be implanted; a xenogeneic cell, i.e., a cell which is from a different species than the recipient into which the cell will be implanted. In the case of an allogeneic cell, the cell can be fully matched or partially matched for MHC class I loci, fully matched or partially matched for MHC class II loci, and fully matched or partially matched for minor loci.

Embodiments of the invention feature the use of coatings, which, result in a decrease in the volume of the coated particle, as is described in PCT/US96/03135 and U.S. patent application Ser. No. 08/402,209, Filed Mar. 10, 1995.

The number of host molecules which can invade a component of a composite microreactor decreases substantially in the inward direction. As is discussed herein, the inner most member of a double composite microreactor is an internal particle. An internal particle is embedded in the next most outermost component, the particle matrix. The particle is in turn embedded in the next most outer component, the supermatrix.

Of source antigens other than the therapeutic substance released from the microreactor, only a small proportion will enter a particle matrix, and only a small proportion of those that enter a particle matrix will be able to be released from the microreactor.

Thus, relatively small members of capture agent molecules, when placed on an outer surface of a microreactor, can have a substantial effect in terms of inactivating source antigens which would otherwise stimulate the host immune system and have a deleterious effect on the implanted cell.

As relatively few source antigen molecules will be released from the microreactor, as compared with the inner most components, e.g., the inner particles, a given number of capture agent molecules will be more efficacious and able to longer avoid saturation by host molecules if they are placed in a more outer component, e.g., the outer surface or even the matrix of a double composite. If a comparable number of capture agent molecules were presented at the inner surface of the inner particle, they would be more rapidly saturated and thus inactivated by the relatively large number of source antigen molecules. However, as each barrier, e.g., coating, or supermatrix or matrix, serially reduces the population of released source antigen molecules, a given number of capture agent molecules can be more efficacious in preserving function.

Of a population of host molecules which invades the supermatrix only a small proportion will be able to enter a particle matrix, and only a small proportion of those that enter a particle matrix will be able to enter an internal particle. Further, relatively small numbers of rescue agent molecules, when placed in an inner component, can have a substantial effect in terms of inactivating host molecules which would otherwise have a deleterious effect on the implanted cells.

As relatively few host molecules will reach the inner components, as compared with the outer most components, e.g., the super matrix, a given number of rescue agent molecules will be more efficacious and able to longer avoid saturation by host molecules if they are placed in a more inner component, e.g., the internal particle or even the particle of a double composite. If a comparable number of rescue agent molecules were presented at the surface of the device, they would be rapidly overwhelmed and thus inactivated by the relatively large number of host molecules. However, as each barrier, e.g., coating, or supermatrix or matrix, serially reduces the population of invading host molecules, a given number of rescue agent molecules are more efficacious in preserving function.

Composite Microreactors

Structural Components

FIG. 1 is a schematic diagram of a simple or single composite microreactor (10). The composite microreactor (10) contains at least one, and preferably a plurality of internal particles (20). An internal particle (20) includes one or a plurality of sources (30) of a therapeutic or otherwise desirable substance. The sources (30) are embedded carried on, adhered to, or in an internal particle matrix (40). The internal particle (20) can optionally include an internal particle coating (50). The internal particles can be embedded in a super matrix (60). The composite microreactor 10 can (optionally) include an outer coating (70).

The diameter of the composite microreactor (10) is preferably between 100 microns and 4 millimeters, between 300 and 1200 microns, between 300 and 1500 microns, between 400 and 1000 microns, or between 400 and 800 microns. More preferably the diameter is about 600 microns.

The diameter of the internal particles (20) before application of a volume-reducing coating (described below) is preferably between 50 and 700 microns, more preferably between 100 and 500 microns, more preferably between 200 and 400 microns, and most preferably about 300 microns in diameter. The diameter of the internal particles (20) after application of a volume-reducing coating (described below) is preferably between 35 and 500 microns, more preferably between 75 and 400 microns, more preferably between 100 and 300 microns, and most preferably about 200 microns in diameter.

As is discussed in more detail elsewhere herein, the source 30 can be a cell, or a group of cells, e.g., an islet. The sources of an internal particle can all be of one type or more than one type of source can be included in an internal particle. Furthermore, the composite microreactor 10 can include more than one type of internal particle (20), e.g., the composite microreactor 10 can include a first type of internal particle (20) having within it a first source, e.g., a first type of cell, and a second type of internal particle (20) having within it a second source, e.g., a second type of cell.

The internal particle matrix (40) can be a gel, e.g., a hydrogel, e.g., alginate or agarose. The internal particle matrix can also be a solid particle, e.g., a glass bead, or a porous structure, on which anchorage dependent cells can be seeded. The internal matrix (40) can have immunoisolative properties. In some embodiments it has little or no ability to exclude low molecular weight species, e.g., release of source antigens or invasion by IgG or complement, with this property being relegated to other components of the composite microreactor (10). The internal particle matrix (40) can be rendered immunoisolating by controlling its porosity, e.g., such that it hinders the passage of molecules of relatively large molecular weight, or by adding to it components, e.g., polyethylene oxide (PEO), polystyrene sulfonic acid (PSA), polyethylene glycol (PEG), or polyornithine (PLO) which hinder the passage of molecules of relatively large molecular weight. Regardless of the method of controlling its permeability, the internal matrix (40) will, in preferred embodiments will hinder the passage, and preferably, essentially completely prevent the passage of: molecules having a molecular weight of more than about 50 kDa, preferably more than about 100 kDa, preferably more than about 150 kDa, and most preferably more than about 400 kDa; or of immune system components such as Ig molecules or complement; or recipient-derived cells. The internal matrix (40) need not be anti-fibrotic and need not be biocompatible. The composite microreactor (10) can include more than one type of internal particle (20), e.g., the composite microreactor (10) can include a first type of internal particle (20) having within it a first type of internal matrix (40) and a second type of internal particle (20) having within it a second type of internal matrix (40).

The internal particle coating (50) is optional. It can be made of a polyamino acid, e.g., polylysine (PLL), PLO, chitosan, or PAN-PVC, or any coating used to coat non-composite microreactors. In addition, the coating can be a formed by modifying the structure of the matrix, e.g., the matrix can be cross-linked, e.g., with metal ions, e.g., Ba or Fe ions, or by photo-cross-linking, to form a coating. A preferred coating is polylysine having a molecular weight of less than 15 kDa, more preferably of less than 10 kDa, more preferably of less than 5 kDa. Particularly preferred are polylysines with a molecular weight of about 3–4 kDa, e.g., 3.7 kDa, or about 9 kDa–10 kDa, e.g., 9.7 kDa. Preferred coatings are volume-reducing coatings. Furthermore, the composite microreactor 10 can include more than one type of internal particle (20), e.g., the composite microreactor 10 can include a first type of internal particle (20) having a first type of internal particle coating and a second type of internal particle (20) having a second type of internal particle coating (50). Because, in some embodiments, the internal particles coating (50) need not be biocompatible and need not be anti-fibrotic, other properties of the internal coating (50), e.g., its ability to immunoisolate, can be optimized without the necessity of any compromise to allow confer biocompatibility or anti-fibrotic activity.

Super matrix (60) can be a gel, e.g., a hydrogel, e.g., alginate or agarose. The super matrix (60) can have immunoisolative properties. In some embodiments it can have little or no ability to exclude low molecular weight species, e.g., IgG or complement, with this property being relegated to other components of the composite microreactor (10). The super matrix (60) can be rendered immunoisolating by controlling its porosity, e.g., such that it hinders the passage of molecules of relatively large molecular weight or by adding to it components, e.g., PEO, PSA, PEG, or PLO which hinder the passage of relatively large molecules. Regardless of the method of controlling its permeability, the super matrix (60) will in preferred embodiments, will hinder the passage, and preferably essentially completely prevent the passage of: molecules having a molecular weight of more than about 50 kDa, preferably more than about 100 kDa, preferably more than about 150 kDa, and most preferably more than about 400 kDa; or of immune system components such as Ig molecules or complement; or recipient-derived cells. The super matrix (60) need not be anti-fibrotic and need not be biocompatible if a more proximal or more exterior component supplies these functions.

A capture agent can be included on the surface of an internal particle (50). A preferred location for a capture agent is the super matrix (60) and an even more preferred location is the outer coating (70). Positioning on the super matrix (60) or on the outer surface (70) allows binding of source antigen molecules before they are released from the microreactor.

Outer coating (70) is optional. It can be made of a polyaminoacid, e.g., PLL or PLO, chitosan, or PAN-PVC, or any coating used to coat non-composite microreactors. Alternatively, the coating can be a formed by modifying the structure of the matrix, e.g., the matrix can be cross-linked, e.g., with metal ions, e.g., Ba or Fe ions, or by photo-cross-linking, to form an coating. A preferred coating is polylysine having a molecular weight of less than 15 kDa, more preferably of less than 10 kDa, more preferably of less than 5 kDa. Particularly preferred are polylysines with a molecular weight of about 3–4 kDa, e.g., 3.7 kDa, or about 9 kDa–10 kDa, e.g., 9.7 kDa. Preferred coatings are volume-reducing coatings. The outer coating (70) need not be immunoisolating if other components supply this function.

The multi-component structure of the composite microreactor allows selection of materials which can optimize performance. Coating materials which are highly immunoisolating, but less desirable in terms of their biocompatibility or anti-fibrotic activities, can be used in the internal particle coating. The multi-component structure also allows for multiple lines of defense against invasion by recipient immune system components. E.g., the use of an outer coating which releases 1 in $10^2$ source antigen molecules, a super matrix which releases 1 in $10^2$ source antigen IgG molecules, and an internal particle coating which releases 1 in $10^2$ source antigen molecules, results in a composite release rate of only about 1 in $10^6$ of the source antigen molecules.

The multi-component structure of composite reactors also allow a rescue agent to be placed in a zone or compartment between the source of a therapeutic substance and the host.

The ability to segregate functions also allows construction of composite microreactors the life of which are roughly commensurate with the useful life of the enclosed sources. For example, gelatin, which weakens the matrix, could be added. If it is necessary to strengthen the matrix, fibers can be added.

A preferred composite microreactor is one in which: the composite microreactor contains at least two internal particles; the source of a therapeutic or otherwise desirable substance is a cell, e.g., an islet cell; the internal particle matrix is alginate; the internal particle includes an internal particle coating of polylysine; the internal particles are embedded in a super matrix of alginate; and the composite microreactor includes an outer coating of polylysine; the polylysine of the internal particle coating is of a molecular weight of between 2 and 10 kDa; the polylysine of the outer coating is of a molecular weight of between 2 and 10 kDa; the internal particles are geometrically stabilized, as is described below; the composite microreactor is generally stabilized, as is discussed in PCT/US96/03135 and U.S. patent appln Ser. No. 08/402,209, Filed Mar. 10, 1995; the super matrix is free of fissures or other defects which arise form the use of internal particles which have not been geometrically stabilized; the diameter of an internal particle, is between 100 and 400 microns, preferably about 200 microns; the diameter of the composite microreactor is between 400 and 800 microns, preferably about 600 microns, and a capture agent is incorporated into the super matrix.

As described above, the internal particle (20) can consist of sources embedded in a matrix, the matrix being enclosed in an internal particle coating. The internal particle (20) can also have other structures. For example, the inner particle can consist of a solid bead, e.g., a plastic bead, a Sepharose bead, (Pharmacia, Piscataway, N.J.) or a glass bead, on which cells, e.g., anchorage dependent cells, are allowed to grow. Cells can be allowed to grow on a surface of the solid bead or, if they are present, within interstitial spaces of the bead. Such an internal particle can be coated as described herein, or left uncoated. The internal particle can be coated or left uncoated. The internal particle, can be embedded in a super matrix, the super matrix being enclosed by coating.

Composite microreactors can also contain fibers or materials to enhance the mechanical strength of the sphere. Similarly, the composite material can contain substances such as PEO or PEG which can act to repel protein and to hinder the fibrotic response. Other materials such as gelatin or collagen can also be added to either increase or decrease the porosity so as to influence the transport properties (permeability/and or molecular weight cutoff).

In addition to advantages, such as ease of retrieval, the embodiments of the invention permit the use of immunoprotectants which are not biocompatible. Materials which alone might be digested by enzymes, or which might trigger a fibrotic response when they come into direct contact with host tissues can be used to form permselective barriers. Methods of the inventor can also be used to alginate-coat particles made of neutral or positively-charged substances. More importantly, the alginate coating furnishes the composite structure with a physical barrier of substantial thickness versus the "coating" formed by mere electrostatic interactions. The composite structure (ranging in diameter from <50 µm to >5 mm) can be made of any material.

Internal particles can be of any shape, including, for example, planar, cubical, tubular, and disk-shaped particles and chambers, or other shapes which might otherwise become fibroencapsulated.

The ratios of the volume of the internal particles to the volume of the composite microreactor can be tailored to particular applications, but preferred ratios are 0.5:5.0, preferably 1.0:3.5, more preferably 1.0:2.5, or 1.0:3.0.

Higher Order Composites

Figure 2:
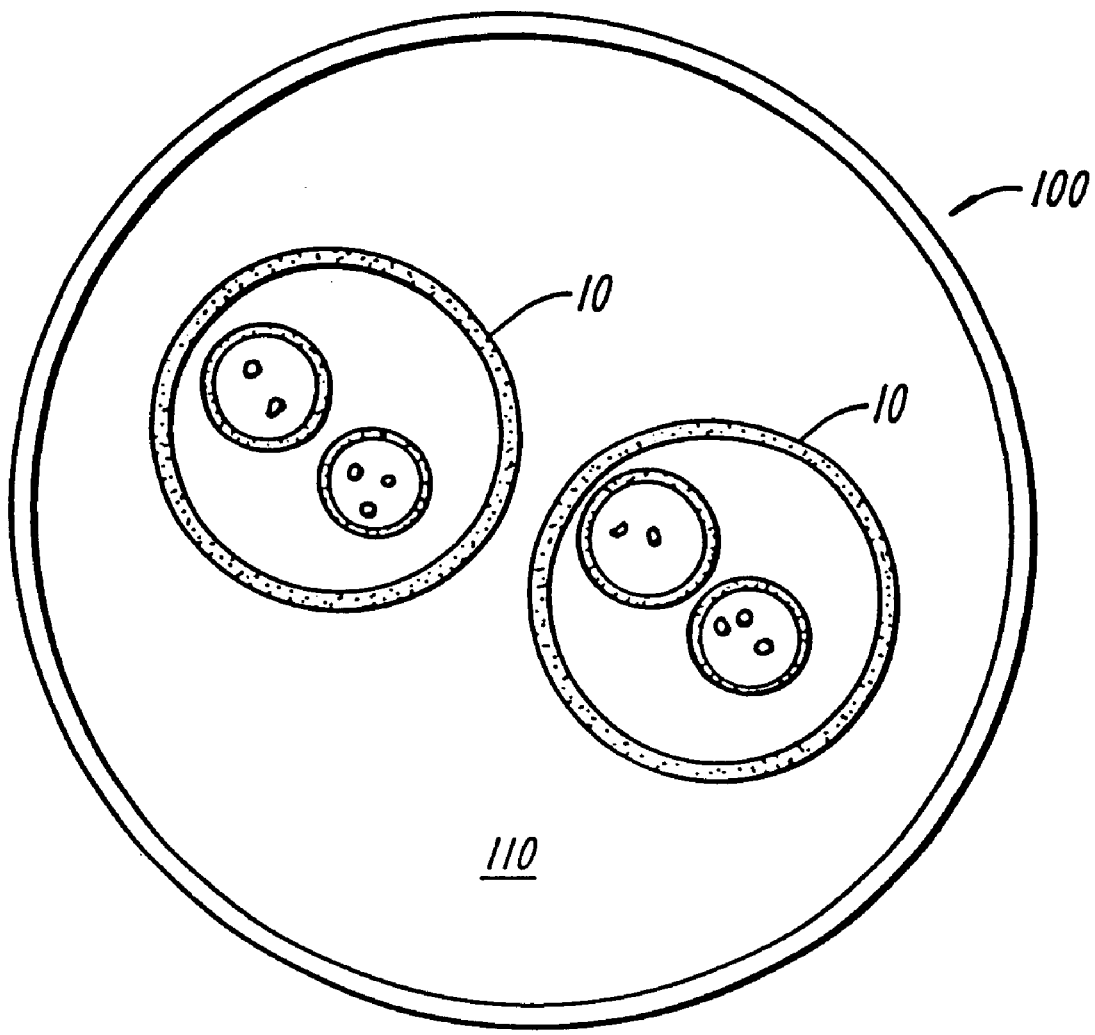
FIG. 2 is a schematic diagram of a double composite microreactor.

Embodiments of the invention include higher order composite microreactors, e.g., a double composite in which single composite microreactors (10) are embedded in a matrix which is (optionally) coated with an outer coating. Accordingly, FIG. 2, shows a second order, or double composite microreactor (100).

The double composite microreactor (100) contains one or a plurality of composite microreactors (10) (as described above and elsewhere herein) embedded in a double composite microreactor matrix or super matrix (110) which is (optionally) enclosed in a double composite microreactor outer coating (120).

The diameter of the double composite microreactor (100) is preferably between 100 microns and 4 millimeters, between 300 and 1500 microns, between 400 and 1000, or between 500 and 900 microns. More preferably the diameter is about 600–800 microns.

Double composite microreactor matrix or super matrix (110) can be a gel, e.g., a hydrogel, e.g., alginate or agarose. The double composite microreactor matrix or super matrix (110) can have immunoisolative properties. In some embodiments it can have little or no ability to exclude low molecular weight species, e.g., IgG or complement, with this property being relegated to other components of the composite microreactor (10). The double composite microreactor matrix or super matrix (110) can be rendered immunoisolating by controlling its porosity, e.g., such that it hinders the passage of molecules of relatively large molecular weight or by adding to it components, e.g., PEO, PSA, PEG, or PLO which hinder the passage of relatively large molecules. Regardless of the method of controlling its permeability, the matrix or super matrix (110) will, in preferred embodiments will hinder the passage, and preferably, essentially completely prevent the passage of molecules having a molecular weight of more than about 50 kDa, preferably more than about 100 kDa, preferably more than about 150 kDa, and most preferably more than about 400 kDa; or of immune system components such as Ig molecules or complement; or recipient-derived cells. The double composite microreactor matrix (110) need not be anti-fibrotic and need not be biocompatible if a more proximal or more exterior component supplies these functions. In double composite, the matrix of the inner most particle is usually referred to as the internal particle matrix. The matrix in which the internal particles are embedded is usually referred to as the particle matrix, and the matrix in which the single composite particles are embedded is usually referred to as the super matrix. A capture molecule can be covalently coupled to a super matrix molecule.

Double composite microreactor outer coating (120) is optional. It can be made of a polyaminoacid, e.g., PLL, PLO, chitosan, or PAN-PVC, or any coating used to coat non-composite microreactors. A preferred coating is a poly amino acid, e.g., polylysine, having a molecular weight of less than 15 kDa, more preferably of less than 10 kDa, more preferably of less than 5 kDa. Particularly preferred are polylysines with a molecular weight of about 3–4 kDa, e.g., 3.7 kDa, or about 9 kDa–10 kDa, e.g., 9.7 kDa. Preferred coatings are volume-reducing coatings. The double composite microreactor outer coating (120) need not be immunoisolating if other components supply this function. A capture agent can be covalently coupled to an outer coating on component.

Other embodiments of the invention include higher order composite microreactors, e.g., third order composites which include double composite microreactors embedded in a matrix and (optionally) enclosed in an outer coating, and forth order composites, which includes third order composites embedded in a matrix and (optionally) enclosed in an outer coating. The materials and methods discussed for use in simple and double composites can be used for the matrices and coatings of higher order composites.

The multicomponent structure of double (or higher order) composites also allows a capture agent to be placed in a zone or compartment which is interposed between the source of a therapeutic substance and the host. E.g., a source of a therapeutic substance can be disposed within the internal particle and one or more capture agents disposed in one or more of the particle matrix or the super matrix zones, or on the outer coating.

Formation of Composite Microreactors

Composite microreactors can be made by materials which are analogous with the methods used to make internal particles: individual or small numbers of internal particles (rather than cells) are embedded in a matrix (referred to herein as a super matrix to distinguish it from the internal particles matrix) and an (optional) outer coating applied.

For example, after the internal particles are prepared and, e.g., either coated or otherwise treated, e.g., cross-linked, they should be washed in medium to prevent the existing microparticles from sticking to each other (particles that have not been coated should be washed in calcium and magnesium free medium), mixed with a liquid hydrogel such as alginate, and formed into a composite microparticle with a diameter from less than 50 µm up to more than 5 mm. For example, in a method which is analogous to that described above for the creation of the internal particles, a mixture of internal particles in a liquid gel can be extruded through an 18 gauge catheter to form composite microreactors.

As is discussed elsewhere herein, it may be desirable to geometrically stabilize the internal particles before incorporating them into a composite microreactor.

The super matrix of a composite microreactor can provide a semipermeable shell of a hydrogel material around all of the encompassed internal particles can provide a physical barrier of substantial thickness compared to the individual coatings on each of the microcapsules. Electrostatic interactions in the super matrix can contribute to immunoisolation.

The super matrix can be made of the same material as the internal particle matrix or it can differ from the matrices of some or all of the internal particle matrices.

A composite microreactor can contain internal particles of any shape, including, for example, planar, cubical, tubular, and disk-shaped particles and chambers, which might otherwise become fibroencapsulated.

A composite microreactor can also contain other substances to modify the properties of the composite microreactor and can, e.g., include fibers or materials in addition to the hydrogel matrix and internal particles to enhance the mechanical strength of the composite microreactor. Similarly, the composite microreactors and particularly the super matrix, can include substances such as PEO or PEG which act to repel proteins and to hinder the fibrotic response. Other materials such as gelatin or collagen can also be added to the super matrix to either increase or decrease the porosity so as to influence the transport properties (permeability and/or molecular weight cutoff) of the composite microreactors.

Higher order composites can be made by analogous methods.

Outer Coating

Composite microreactors can (optionally) be provided with an outer coating. Although any coating used with non-composite microreactors or for internal particles can be used for the outer coating, other coatings, or no coating, can be used as well. Because the various properties need by the implanted device, e.g., biocompatibility, the ability to resist fibrotic encapsulation, the ability to prevent recipient immune inactivation of the implanted donor tissue, can be distributed among the various components of the composite microreactor, the outer coating need not supply all of these properties. It may be desirable to geometrically stabilize the supermatrix prior to application of a coating.

Pretreatment of Microreactors

As discussed herein, the therapeutic source, e.g., implanted tissue, e.g., islet cells or other pancreatic tissue, can release antigens which can escape from an implantable device and elicit a host immune response. The number of antigens is, in many cases, greater when the cells are first encapsulated than over time. Thus, a microreactor or a component thereof, which contains a source of a therapeutic substance can be aged or incubated for a period of time sufficient to permit release or shedding of antigens prior to incorporating a capture agent into the microreactor. The incubation period allows for the release of antigen prior to inclusion of the capture agent thereby preventing saturation or occupation of capture agents and increasing the usefull lifetime of the microreactor. By providing a microreactor which releases fewer antigens, the ratio of released antigen molecules to capture agents is improved. In the case where the capture agent, e.g., a monoclonal antibody, is adhered or coupled to the outer coating of a microreactor or an internal component of the microreactor or to particles immobilized within the microreactor or to an outer PLL coating of the microreactor, the component containing the therapeutic source can be assembled and aged for a sufficient period of time to allow release of antigen, for example, for at least 10, 20, 30, 40 or 50 days. After a period of aging or incubation, the capture agent is added to the microreactor or component. In the case of a composite microreactor wherein the source is located in the internal particle, the internal particle can be manufactured and aged for a sufficient amount of time and then incorporated into a matrix in which the capture agent is placed. In the case of a microreactor where the capture agent is adhered or coupled to the outer PLL coating of the microreactor, the microreactor can be assembled and aged for sufficient time prior to attaching a capture agent to the surface. The initial experiments with swine islet cells suggest that as much as about 80% of the antigen from the islet cells is released from the microreactor within the first fourteen days and after an incubation period of 23 days about 90% of the antigens on the surface of the islet cells is released.

Preincubation of microreactors prior to introduction into a recipient can also be used with microreactors which do not include a capture agent. In this case, a microreactor or a component thereof is aged for a sufficient time to allow release of a substantial amount of antigen. For example, it is aged for at least 10, 20, 30, 40 or 50 days. These methods can be used for any of the microreactors described herein which do not contain a capture agent. In fact, pretreatment to release antigen from a therapeutic source can be used with any microreactor or implantable device which would otherwise release antigen and impair the lifetime of the device.

Preparation of Antibody Capture Agents

Immunization

Antibodies which elicit minimal response in a human recipient can be made, e.g., by producing a human monoclonal antibody directed against non-therapeutic, source-derived substance generated in transgenic mice or in immune deficient mice engrafted with antibody-producing human cells. Such methods include raising antibody in transgenic mice which express human immunoglobin genes (see, e.g., Wood et al. PCT publication WO 91/00906, Kucherlapati et al. PCT publication WO 91/10741; Lonberg et al. PCT publication WO 92/03918; Kay et al. PCT publication WO 92/03917; Kay et al. PCT publication WO 93/12227; Kay et al. PCT publication 94/25585; Rajewsky et al. Pct publication WO 94/04667; Ditullio et al. PCT publication WO 95/17085; Lonberg, N. et al. (1994) Nature 368:856–859; Green, L. L. et al. (1994) Nature Genet. 7:13–21; Morrison, S. L. et al. (1994) Proc. Natl Acad. Sci. USA 81:6851–6855; Bruggeman et al. (1993) Year Immunol 7:33–40; Choi et al. (1993) Nature Genet. 4:117–123; Tuaillon et al. (1993) PNAS 90:3720–3724; Bruggeman et al. (1991) Eur J Immunol 21:1323–1326). In addition, human monoclonal antibodies can be produced by introducing an antigen into immune deficient mice which have been engrafted with human antibody-producing cells or tissues (e.g., human bone marrow cells, peripheral blood lymphocytes (PBL), human fetal lymphnode tissue, or hematopoietic stem cells). Such methods include raising antibody in SCID-hu mice (see Duchosal et al. PCT publication WO 93/05796; U.S. Pat. No. 5,411,749; McCune et al. (1988) Science 241:1632–1639), Bg/Nu/Xid mice (see Kamel-Reid et al. (1988) Science 242:1706), Rag-1 deficient mice (see, e.g., Spanopoulou (1994) Genes & Development 8:1030–1042) Rag-2 deficient mice (see e.g., Shinkai et al. (1992) Cell 68:855–868) or Rag-1/Rag-2 deficient mice. Human antibody-immune deficient mice are also commercially available. For example, Rag-2 deficient mice are available from Taconic Farms (Germantown, N.Y.). A human antibody-transgenic mouse or an immune deficient mouse engrafted with human antibody-producing cells or tissue can be immunized with a source-derived, non-therapeutic immunogen and splenocytes from these immunized mice can then be used to create hybridomas.

The unit dose of immunogen (i.e., a non-therapeutic component from the donor source) and the immunization regimen will depend upon the species of mammal immunized, its immune status and the body weight of the mammal. To enhance to immune response in the subject, an immunogen can be administered with an adjuvant, such as Freund's complete or incomplete adjuvant.

Immunization of a subject with an immunogen as described above induces polyclonal antibody response. The antibody titer in the immunized subject can be monitored over time by standard techniques such as a ELISA using immobilized antigen. If desired, capture antibodies directed against a non-therapeutic protein can be isolated from the immunized subject (e.g., from the blood) and further purified by well known techniques such as protein A chromatography to obtain an IgG fraction. At the appropriate time after immunization, e.g., when the antibody titers are highest, antibody producing cells can be harvested from an immunized animal and used to prepare monoclonal antibodies. The antibody producing cells can be fused by standard somatic cell fusion procedures with immortalizing cells such as myeloma cells to yield hybridoma cells. Such techniques are well known in the art, an include, for example, the hybridoma technique as originally developed by Kohler and Milstein, (1975) Nature, 256: 495–497), the human B cell hybridoma technique (Kozbar et al., (1983) Immunology Today, 4:72), and the EBV-hybridoma technique to produce human monoclonal antibodies (Cole et al., (1985) Monoclonal Antibodies and Cancer Therapy, Alan R. Liss, Inc. pp. 77–96).

Hybridomas

Human splenocytes, such as those obtained from the immune deficient mice described above, can be immortalized through fusion with human myelomas or through transformation with Epstein-Barr virus (EBV). These human hybridomas can be made using human B cell- or EBV-hybridoma techniques described in the art (see, e.g., Cole et al., supra; Boyle et al. European Patent Publication 0 614 984).

Hybridoma cells producing a monoclonal antibody of the invention are detected by screening the hybridoma culture supernatants by, for example, screening to select antibodies that bind immobilized proteins or peptides from the source (e.g., porcine SLA class I antigen).

Hybridoma cells that test positive in the above screening assays can be cultured in a nutrient medium under conditions and for a time sufficient to allow the hybridoma cells to secrete the monoclonal antibodies into the culture medium, to thereby produce whole antibodies. Tissue culture techniques and culture media suitable for hybridoma cells are generally described in the art (see, e.g., R. H. Kenneth, in *Monoclonal Antibodies: A New Dimension In Biological Analyses,* Plenum Publishing Corp., New York, N.Y. (1980); E. A. Lerner (1981) *Yale J Biol. Med.,* 54:387–402). Conditioned hybridoma culture supernatant containing the antibody can then be collected.

Recombinant Combinatorial Antibody Libraries

Monoclonal antibodies which are engineered to minimize the response by a human host can be prepared by constructing a recombinant combinatorial immunoglobulin library, such as a Fab phage display library or a scFv phage display library, using immunoglobulin light chain and heavy chain cDNAs prepared from mRNA derived from lymphocytes of a subject. For example, human antibody fragments with binding antivity against a non-therapeutic source derived substance can be isolated from repertoires of rearranged variable genes derived from the mRNA of PBL from unimmunized humans. See McCafferty et al. PCT publication WO 92/01047; Marks et al. (1991) *J Mol. Boil.* 222:581–597; and Griffths et al. (1993) *EMBO J* 12:725–734. Briefly, mRNA is isolated from a lymphocyte-containing cell population, such as PBL. First-strand cDNA is synthesized using primers specific for a constant region of the heavy chain and the constant region of each of the κ and λ light chains. Using primers specific for the variable and joining (or constant) regions, the heavy and light chain cDNAs are amplified by the polymerase chain reaction (PCR).

In certain embodiments, V-genes are assembled at random to encode repertoires of single chain Fv fragments by PCR with a polypeptide linker. The V region domains of heavy and light chains can be expressed on the same polypeptide, joined by a flexible linker to form a single-chain Fv fragment, and the scFv gene subsequently cloned into the desired expression vector or phage genome. As generally described in McCafferty et al., *Nature* (1990) 348:552–554, complete VH and VL domains of an antibody, joined by a flexible $(Gly_4\text{-}Ser)_3$ linker can be used to produce a single chain antibody expressed on the surface of a display package, such as a filamentous phage.

The amplified DNA is then ligated into appropriate vectors for further manipulation in generating a library of display packages.

Oligonucleotide primers useful in amplification protocols may be unique or degenerate and may incorporate inosine at degenerate positions. Restriction endonuclease recognition sequences may also be incorporated into the primers to allow for the cloning of the amplified fragment into a vector in a predetermined reading frame for expression.

Another method which can be used to prepare an antibody fragment which displays minimal response by a human host is to generate combinatorial library of antibody variable regions by mutating a known human antibody. For example, a variable region of a human antibody known to bind an antigen which is capable of eliciting an immune response, e.g., an MHC class I or class II gene, can be mutated, by for example using degenerate oligonucleotides, to generate a library of mutated variable regions which can then be screened to bind to a related antigen from the source, e.g., the source is porcine islet cells and the antigen is SLA class I or class II.

In particular, methods of inducing random mutagenesis within the CDR regions of immunoglobin heavy and/or light chains, methods of crossing randomized heavy and light chains to form pairings and screening methods can be found in, for example, Barbas et al. PCT publication WO 96/07754; Barbas et al. (1992) *Proc. Nat'l Acad. Sci USA* 89:4457–4461.

The immunoglobulin library, e.g., a scFv fragment library, is expressed by a population of display packages, preferably derived from filamentous phage, to form an antibody display library. Ideally, the display package comprises a system that allows for the sampling of a large, diverse antibody display library, rapid sorting after each affinity separation round, and easy isolation of the antibody genes from the purified display packages. In addition to commercially available kits for generating phage display libraries (e.g., the Pharmacia *Recombinant Phage Antibody System,* catalog no. 27-9400-01; and the Stratagene SurfZAP™ phage display kit, catalog no. 240612), examples of methods and reagents particularly amenable for use in generating antibody display library can be found in, for example, Ladner et al. U.S. Pat. No. 5,223,409; Kang et al. PCT publication WO 92/18619; Dower et al. PCT publication WO 91/17271; Winter et al. PCT publication WO 92/20791; Markland et al. PCT publication WO 92/15679; Breitling et al. PCT publication WO 93/01288; McCafferty et al. PCT publication WO 92/01047; Garrard et al. PCT publication WO 92/09690; Ladner et al. PCT publication WO 90/02809; Fuchs et al. (1991) *Bio/Technology* 9:1370–1372; Hay et al. (1992) *Hum Antibod Hybridomas* 3:81–85; Huse et al. (1989) *Science* 246:1275–1281; Griffths et al. (1993) supra; Hawkins et al. (1992) *J Mol Biol* 226:889–896; Clackson et al. (1991) *Nature* 352:624–628; Gram et al. (1992) *PNAS* 89:3576–3580; Garrad et al. (1991) *Bio/Technology* 9:1373–1377; Hoogenboom et al. (1991) *Nuc Acid Res* 19:41334137; and Barbas et al. (1991) *PNAS* 88:7978–7982.

Once displayed on the surface of a display package (e.g., filamentous phage), the antibody library is screened to identify and isolate packages that express an antibody that binds a non-therapeutic peptide from the therapeutic source, for example MHC class I or class I antigens. In a preferred embodiment, the primary screening of the library involves panning with an immobilized antigen derived from the therapeutic source, preferably an MHC class I or class II antigen. Display packages expressing antibodies that bind immobilized antigen are selected.

Reagents usefull for screening antibodies of the invention can include proteins or peptides which are known to stimulate am immune response in an allogenic or xenogenic host recipient. For example, MHC class I or class II antigens can be used to screen antibodies produced by phage.

Following screening and isolation of a monoclonal antibody of the invention from a recombinant immunoglobulin display library, nucleic acid encoding the selected antibody can be recovered from the display package (e.g., from the phage genome) and subcloned into other expression vectors by standard recombinant DNA techniques. The nucleic acid can be further manipulated (e.g., linked to nucleic acid encoding additional immunoglobulin domains, such as additional constant regions)and/or expressed in a host cell.

Chimeric and Humanized Antibodies.

Recombinant forms of antibodies, such as chimeric and humanized antibodies, can also be prepared to minimize the response by a human host to a capture agent antibody. When antibodies produced in non-human subjects or derived from expression of non-human antibody genes are used therapeutically in humans, they are recognized to varying degrees as foreign and an immune response may be generated in the recipient. One approach for minimizing or eliminating this problem is to produce chimeric antibody derivatives, i.e., antibody molecules that combine a non-human animal variable region and a human constant region. Such antibodies retain the epitope binding specificity of the original monoclonal antibody, but may be less immunogenic when administered to humans, and therefore more likely to be tolerated by the patient.

Chimeric monoclonal antibodies can be produced by recombinant DNA techniques known in the art. For example, a gene encoding the constant region of a non-human antibody molecule is substituted with a gene encoding a human constant region. (see Robinson et al., PCT Patent Publication PCT/US86/02269; Akira, et al., European Patent Application 184,187; Taniguchi, M., European Patent Application 171,496; Morrison et al., European Patent Application 173,494; Neuberger et al., PCT Application WO 86/01533; Cabilly et al. U.S. Pat. No. 4,816,567; Cabilly et al., European Patent Application 125,023; Better et al. (1988 *Science* 240:1041–1043); Liu et al. (1987) *PNAS* 84:3439–3443; Liu et al. (1987) *J Immunol* 139:3521–3526; Sun et al. (1987) *PNAS* 84:214–218; Nishimura et al. (1987) *Canc. Res.* 47:999–1005; Wood et al. (1985) *Nature* 314:446449; and Shaw et al. (1988) *J. Natl Cancer Inst.* 80:1553–1559).

A chimeric antibody can be further "humanized" by replacing portions of the variable region not involved in antigen binding with equivalent portions from human variable regions. General reviews of "humanized" chimeric antibodies are provided by Morrison, S. L. (1985) *Science* 229:1202–1207 and by Oi et al. (1986) *BioTechniques* 4:214. Such methods include isolating, manipulating, and expressing the nucleic acid sequences that encode all or part of an immunoglobulin variable region from at least one of a heavy or light chain. The cDNA encoding the humanized chimeric antibody, or fragment thereof, can then be cloned into an appropriate expression vector. Suitable "humanized" antibodies can be alternatively produced by CDR or CEA substitution (see U.S. Pat. No. 5,225,539 to Winter; Jones et al. (1986) *Nature* 321:552–525; Verhoeyan et al. (1988) *Science* 239:1534; and Beidler et al. (1988) *J Immunol.* 141:4053–4060).

Epitope imprinting can also be used to produce a "human" antibody polypeptide dimer which retains the binding specificity of a murine antibody specific for an antigen. Briefly, a gene encoding a non-human variable region (VH) with binding specificity to an antigen and a human constant region (CH1) is expressed in *E. coli* and infected with a phage library of human Vλ.Cλ. genes. Phage displaying antibody fragments are subject to panning with the antigen. Selected human Vλ genes are recloned for expression of V λCλ chains and *E. coli* harboring these chains are infected with a phage library of human VHCH1 genes and the library is subject to rounds of panning with antigen coated tubes. See Hoogenboom et al. PCT publication WO 93106213.

Coupling Technologies for Cross-linking a Capture Agent to an Implantable Device Component In many cases the immunoisolating properties of the implantable device, together with the size and other physical characteristics of the capture agent will insure that the capture agent is held within the implantable device. In some embodiments, though, it is desirable to link the capture agent to another entity, to increase its size, to anchor it within the implantable device, to maintain it within a compartment of an implantable device or to otherwise inhibit its diffusion out of the device.

Capture agents can be bound to carrier molecules, insoluble substrates, or to other components of an implantable device. Capture agent ligands can be coupled to these entities by procedures known to one of ordinary skill in the art.

The term "coupling agent" as used herein, refers to a reagent capable of coupling or cross-linking a capture agent to another component, e.g., to an implantable device component. Any bond which is capable of linking the components such that they are stable under physiological conditions for the time needed for administration and treatment is suitable, and covalent linkages are preferred. A coupling agent should function under conditions of temperature, pH, salt, solvent system, and other reactants that substantially retain the chemical stability of the capture agent. Coupling is preferably performed prior to encapsulation of the biological material.

A coupling agent can link components without elements of the coupling agent remaining added to the final components of the implantable device. Another coupling agent can cause the addition of a molecular element of the coupling agent to the linked components. For example, a coupling agent can be a cross-linking agent that is a homo- or hetero-bifunctional molecule, wherein one or more atomic components of the agent can be retained in the composition. A coupling agent that is not a cross-linking agent can be removed entirely during the coupling reaction, so that the molecular product can be composed entirely of the capture agent and the coupled component.

Many coupling agents react with an amine and a carboxylate, to form an amide, or an alcohol and a carboxylate to form an ester. Coupling agents are known in the art, see, e.g., M. Bodansky, "Principles of Peptide Synthesis", 2nd ed., referenced herein, and T. Greene and P. Wuts, "Protective Groups in Organic Synthesis," 2nd Ed, 1991, John Wiley, NY. Coupling agents should link component moieties stably such that there is only minimal or no denaturation or deactivation of the capture agent, which in general can be more labile to conditions of temperature, pH, salt, and non aqueous solvent, than is the more stable implantable device component.

A variety of coupling agents, including cross-linking agents, can be used for covalent conjugation. Examples of cross-linking agents include N,N'-dicyclohexylcarbodiimide (DCC; Pierce), N-succinimidyl-S-acetyl-thioacetate (SATA), N-succinimidyl-3-(2-pyridyldithio)propionate (SPDP), ortho-phenylenedimaleimide (o-PDM), and sulfosuccinimidyl 4-(N-maleimidomethyl) cyclohexane-1-carboxylate (sulfo-SMCC). See, e.g., Karpovsky et al. *J Exp. Med.* 160:1686, 1984; and Liu, MA et al., *Proc. Natl. Acad. Sci. USA* 82:8648, 1985. Other methods include those described by Paulus, *Behring Ins. Mitt.*, No. 78, 118–132, 1985; Brennan et al. *Science* 229:81–83, 1985, and Glennie et al., *J Immunol.*, 139: 2367–2375, 1987. A large number of coupling agents for peptides and proteins, along with buffers, solvents, and methods of use, are described in the Pierce Chemical Co. catalog, pages T-155 -T-200, 1994 (3747 N. Meridian Rd., Rockford Ill., 61105, U.S.A.; Pierce Europe B.V., P.O. Box 1512, 3260 BA Oud Beijerland, The Netherlands), which catalog is hereby incorporated by reference.

DCC is a useful coupling agent (Pierce #20320; Rockland, Ill.). It promotes coupling of the alcohol NHS to another entity in DMSO (Pierce #20684), forming an activated ester which can be cross-linked to polylysine. DCC (N,N'-dicyclohexylcarbodiimide) is a carboxy-reactive cross-linker commonly used as a coupling agent in peptide synthesis, and has a molecular weight of 206.32. Another useful cross-linking agent is SPDP (Pierce #21557), a heterobifunctional cross-linker for use with primary amines and sulfhydryl groups. SPDP has a molecular weight of 312.4, a spacer arm length of 6.8 angstroms, is reactive to NHS-esters and pyridyldithio groups, and produces cleavable cross-linking such that, upon further reaction, the agent is eliminated so the capture agent can be linked directly to the microcapsular component. Other useful conjugating agents are SATA (Pierce #26102) for introduction of blocked SH groups for two-step cross-linking, which is deblocked with hydroxylamine-HCl (Pierce #26103), and sulfo-SMCC (Pierce #22322), reactive towards amines and sulfhydryls. Other cross-linking and coupling agents are also available from Pierce Chemical Co. (Rockford, Ill.). Additional compounds and processes, particularly those involving a Schiff base as an intermediate, for conjugation of proteins to other proteins or to other compositions, for example to small molecules, for example, such as lazaroids or chelators, are disclosed in EPO 243,929 A2 (published Nov. 4, 1987).

Peptides and other agents which contain carboxyl groups can be joined to lysine ϵ-amino groups in one of the implantable device coatings either by preformed reactive esters (such as N-hydroxy succinimide ester) or esters conjugated in situ by a carbodiimide-mediated reaction. The same applies to capture agents which contain sulfonic acid groups, which can be transformed to sulfonyl chlorides which react with amino groups. Capture agents which have carboxyl groups can be joined to amino groups on a polypeptide by an in situ carbodiimide method. Capture agents can also be attached to hydroxyl groups, of serine or threonine residues or to sulfhydryl groups, of serine or threonine residues or to sulfhydryl groups of cysteine residues.

See, "Short Protocols in Molecular Biology", Ed. F. Ausubel, 3rd Ed., 1995, Wiley, for the use of cyanogen bromide (CNBr)-activated Sepharose. CNBr pre-activated beads are available (Pharmacia Biotech, Piscataway, N.J.). Anti-IgG serum fractions can be obtained commercially also (Zymed Laboratories, South San Francisco, Calif.).

Methods of the invention reduce or eliminate the need for immunosuppression in a recipient subject. In some instances, limited administration of immunosuppressive agents can be desirable. Immunosuppressive treatment can include: administering to the recipient adjunctive immunosuppression for less than one year, 180 days, 90 days, 60 days, or 30 days; administering a drug to the host animal at a dosage effective to inhibit fibrosis and inflammation around the uncoated particle, but at a dosage lower than that required to achieve the same effect when a rescue agent is not used. For example, cyclosporin A can be administered at a dosage that achieves a whole blood trough level of less than about 100 ng/ml in the host animal.

Rescue Agents

Devices of the invention can also include rescue agents.

Rescue agents are molecules (or in some cases cells) which can inhibit the ability of a host molecule to damage donor, e.g., implanted tissue. (Donor tissue is used herein to refer to tissue which is implanted into a host or recipient. Donor tissue also refers to tissue used in an extra-corporeal device, even though it is not implanted in the recipient or host.) Rescue agents can act by absorbing, adsorbing, binding, degrading, sequestering, neutralizing, or otherwise inhibiting a molecule elaborated by the host.

In preferred embodiments, in the case of an implanted device, the host molecules enter the device and interact with a rescue agent within the implanted device. In other embodiments, a rescue agent is, e.g., an anti-fibrotic or an anti-macrophage agent, released by the implanted device into the host, though in most cases the rescue agent will be contained within the device and not released.

Devices, e.g., implantable or extracorporeal devices, of the invention include a source of a therapeutic substance. The rescue agent is a different molecule than the therapeutic substance.

A rescue agent can have a relatively high and specific affinity for a host molecule, e.g., it can have an affinity and specificity similar to that of an antibody for its antigen, an enzyme for its substrate, or a cell surface receptor for its ligand. Other rescue agents have a relatively low specificity and affinity, e.g., an affinity and specificity similar to that of protein A, protein C, or human serum albumen.

A rescue agent can be, for example, a peptide, a non-peptide molecule, or a cell. Although a rescue agent can be a cell, in preferred embodiments it is not a cell, e.g., it is a molecule.

An example of a peptide rescue agent is an antibody which binds a host molecule, for example, an antibody which binds a host antibody such as a host IgG, IgA, IgM, or IgE. The antibody can be directed against a constant region of the host antibody. The host antibody can be reactive with the source of the therapeutic substance, or for a component of the device.

An antibody rescue agent can be directed against a component of the host complement system, for example, against host C3, C3b, Factor B, Factor D, or properdin, or a host protein that activates Factor B, Factor D, or properdin.

Antibody rescue agents can also be directed against other host proteins, e.g., inflammatory molecules, e.g., inflammatory cytokines, e.g., TNF-α, TNF-β, IL-1β, IL-6 or gamma interferon.

An antibody rescue agent can be a monoclonal antibody or a polyclonal antibody, a chimeric antibody, a humanized antibody, a single chain antibody, or a fragment derived from such antibodies.

A peptide rescue agent can be a protein which is not an antibody. A preferred embodiment of a non-antibody peptide rescue agent is an anti-inflammatory cytokine, for example, an anti-inflammatory interleukin, for example, IL-4, IL-10, or IL-13. The anti-inflammatory cytokines of the invention should be specific to the host. Other such agents include the IL-1 receptor agonist.

A non-antibody polypeptide rescue agent can be a polypeptide which binds an unwanted host molecule, reversibly or irreversibly. Examples of such rescue agent ligands can be receptors, or fragments thereof, which bind molecules elaborated by the host, e.g., host molecules which propagate an impure or inflammatory response. Preferred examples are receptors, or fragments thereof, which bind inflammatory cytokines, for example, molecules which can bind TNF-α or TNF-β, IL-1β, IL-6, or gamma interferon. Other examples of such rescue agents include: ligands which bind enzymes, for example, nitric acid synthase, Additional rescue agents of protein or peptide nature include: a naturally-occurring or an engineered cytokine binding protein, such as TNF BP-I; an antibody to an inflammation-related enzyme, such as anti-host neutrophil myeloperoxidase; an engineered inhibitory binding protein to a host enzyme; a naturally occurring complement inhibitor such as Factor H or a soluble form of CDAF; an engineered complement binding-protein or inhibitor; or an enzyme that neutralizes an inflammatory substance, such as superoxide dismutase which reduces a superoxide anion.

A rescue agent can be naturally occurring molecule, or fragment or analog thereof, or a synthetic binding agent engineered by recombinant or protein engineering technologies. These include artificial epitope analogs, e.g., α-gal epitopes and synthesized artificial ligands, e.g., ligands discovered through phage display or other screening methods.

A rescue agent can be a non-peptide substance having an affinity for an unwanted host cell molecule, for example, a dextran blue bead or a DEAE-Affigen blue resin which has affinity for an antibody molecule. Another embodiment of a non-peptide rescue agent is an anti-inflammatory steroid, for example, a 23-amino steroid, for example a lazaroid.

A rescue agent can be a cell which produces or releases a rescue agent, for example, a peptide rescue agent discussed herein; for example, a red blood cell which can be used to rescue tissue from damaging effects of nitric oxide, or a leukocyte which produces an anti-inflammatory cytokine. A rescue agent can be an engineered cell, for example, an autologous allogeneic or xenogeneic cell engineered to release a rescue agent. In preferred embodiments where the rescue agent is a cell it is other than a red blood cell.

Rescue agents are particularly useful against host immune molecules. Molecules elaborated by the immune system which, despite the semipermeable or even immunoisolating properties of the device, can enter the device and have the effect of rejecting or being toxic to the biological material encapsulated in the device. Rejection of the tissues or cells of the biological material can be mediated by one or more components of the host immune system, such as cytokines, antibodies, complement, or other enzymes, or small molecules such as histamine. Each of these classes of agents that cause host immune rejection of implanted material can have their activity modulated by rescue agents.

A rescue agent for host immune rejection is an agent capable of protecting the encapsulated biological material from immune rejection by the host. The immune system can reject a foreign material by a variety of mechanisms involving antibody-independent pathways, such as by the action of the alternative complement pathway, or by a degranulation product of a leukocyte, for example a neutrophil. Products of neutrophil degranulation include enzymes, histamines, and reactive superoxide anions. The immune system can also reject a foreign material by an antibody-dependent process, stimulated by the binding of a molecule of an IgG, an IgM, an IgA or a molecule of another antibody isotype to an implantable device component.

Rescue agents should be non-toxic both to the biological material of the device, and to the host. The rescue agent should reduce or eliminate the activity of unwanted host molecules without substantially affecting release of the biological substance, such as insulin or thyroxin, generated by the implanted device for the benefit of the host.

In many embodiments the rescue agent is maintained within an implanted device in a stable, active form during the lifetime of the implanted device; if the rescue agent is to be released from an implanted device the pharmacokinetics of release be suitable to the kinetics of host immune rejection of the implanted device.

Further, if release from an implanted device is not desired, for example a rescue agent that is a purified preparation of a anti-IgG, for use to capture host antibody ligands, the rescue agent should be stably contained or immobilized in one or more compartments of the implanted device. This can be done by disposing semipermeable barriers between the rescue agent and the host or by coupling the rescue agent to a component of the device.

Incorporation of anti-human antibodies into a implantable device can function as a rescue agent by binding to a host antibody molecule, e.g., a host antibody elaborated against one or more components of the implanted device, or elaborated against one or more components released by the biological material, for example, a porcine islet encapsulated in the implanted device.

As referred to above, an anti-inflammatory therapeutic agent, for example, a lazaroid (see, for example, Villa, R. et al., 1997, Pharmacolog. Rev. 49: 999–136) can be used as a rescue agent. The lazaroid U-74500A is a 21 -aminosteroid capable of inhibiting cytotoxicity and lipid peroxidation. This lazaroid reduces hydrogen peroxide generation by neutrophils and by monocytes, and can inhibit neutrophil infiltration and resultant tissue myeloperoxidase activity (Tanaka, H. et al. 1997, J. Amer. Coll. Surgeons 184: 389–396). Further, lazaroids can act synergistically with penicillamine to protect against peroxynitrite (ONOO–; Fici, G. et al., 1997, Free Radical Biol. & Med., 22: 223–228). The lazaroid U83836E protects hepatocytes from bile salt-induced apoptosis (Patel, T. et al., 1997, Toxicol. Appl. Pharmacol. 142: 116–122), and protects mesencephalic neurons from nitric oxide death (Grasbon-Frodl, E. et al., 1997, Exp. Brain Res. 113: (38–143).

Rescue agents can be provided by cells which naturally produce them or by cells which have been gradually engineered to produce the rescue agent. The cells are included in one or more compartments of an implantable device.

An example of a rescue agent-producing cell is a hybridoma cell, capable of expressing and secreting a gene encoding a rescue agent immunoglobin protein. For example, a rescue agent can be an encapsulated mouse hyridoma cell which is capable of producing an IgG molecule with affinity for an epitope on a host IgG molecule. A rescue agent can be an encapsulated cell that produces an anti-inflammatory cytokine, for example, IL-13.

Transfection and culture of cells with a gene encoding the human TNF type I receptor, or a soluble domain of this receptor, resulting in expression of a TNF binding protein (TBP-I) are disclosed in European Patent 433 900 A1. U.S. Pat. No. 5,512,544 (European Patent 512 528 A2) discloses that TBPs are useful in treatment of autoimmune diseases and graft-versus-host reactions.

The invention is further illustrated by the following examples, which should not be construed as further limiting.

The contents of all references, pending patent applications and published patents, cited throughout this application, are hereby expressly incorporated by reference.

Implantation

Implantable devices can be implanted by methods known to those skilled in the art. The implantable devices can be implanted into a host by injection with a standard catheter or syringe, e.g., with a 16 gauge needle for beads less than 1000 $\mu$m in diameter. Larger implantable devices can be inserted via a small incision, e.g., with a catheter or funnel-like device. The beads are preferably implanted into the host intraperitoneally. The beads can also be implanted intramuscularly or subcutaneously. Alternatively, the beads can also be implanted into immunoprivileged sites such as the brain, testes, or thymus, where the host's immune response is least vigorous, as described in Chapter 7 of Lanza et al. (eds.), *Immunomodulation of Pancreatic Islets* (RG Landes, Tex., 1994). Composite implantable devices can also be introduced at a site where the substance provided by the composite implantable device is needed locally. E.g., a implantable device which provides $\alpha$-interferon could be implanted in tumors. The implantable devices of the invention can be delivered to a subcutaneous site. The composite implantable devices can be inserted through a small surgically created opening using a gun/trocar type device that slips the beads under the skin.

A suitable host for the invention can be a subject or a patient, sometimes referred to as "recipient." The term "subject," as used herein, refers to a living animal or human in need of therapy for, or susceptible to, a condition, which is remediable through implantable device implantation and reduction of potential host immune rejection of the implantable device. In preferred embodiments, the subject is a mammal, including humans and non-human mammals such as dogs, cats, pigs, cows, sheep, goats, horses, rats, and mice. In the most preferred embodiment, the subject is a human. The term "subject" does not preclude individuals that are normal in all respects. The subject can be a candidate for future treatment by microcapsular implantation, formerly have been treated surgically or by chemotherapy, and can be under treatment by microcapsular implantation, and can have been so treated in the past.

The term "patient," as used herein, refers to a human subject who has presented at a clinical setting with a particular symptom or symptoms suggesting treatment by implantation of implantable devices and suppression of the immune response concomitant to or subsequent to implantation. A patient's diagnosis can alter during the course of disease progression, such as development of further disease symptoms, or remission of the disease, either spontaneously or during the course of a therapeutic regimen or treatment.

EXAMPLES

Example 1: Retention of Antibody Molecules in an Alginate Implantable Device

Alginate (Pronova LVG sodium alginate, Protan, Drammen, Norway) implantable devices, 600 $\mu$m diameter, were produced and an implantable device sample was incubated for 90 min at room temperature in a solution of guinea pig antibody to pig insulin (Sigma Immunochemicals, St. Louis, Mo.). Poly-L-lysine (PLL; Sigma) of molecular weight 3.9 kD at 0.2% concentration was used to coat the microreactors, followed by 0. 15% UP alginate, then by another layer of 0.2% PLL. At 3 days after formation and antibody inclusion, implantable devices with anti-pig insulin antibody, and control implantable devices lacking antibody, were incubated with $^{125}$I-insulin (NEN Radiochemicals, Billerica, Mass.) for 2 h, washed several times, and radioactivity of samples where determined in a Cobra 5010 Packard counter.

Data in Table 1 show that over 96% of initial radioactivity in antibody-containing implantable devices is retained on day 2, 95% is retained on day 3, and 94% on day5.

The decline in radioactivity, uncompensated for $^{125}$I decay with a 60 d half-life, can reflect several dynamic biochemical processes: leakage of antibody from the implantable device; dissociation of antigen from antibody at the characteristic rate of the affinity constant; and denaturation of the antibody. The data show clearly that microencapsulated antibody molecules are retained to a statistically significant extent.

TABLE 1

Retention of labeled insulin by anti-insulin antibody-bearing implantable devices.

| Time (days) after insulin exposure | Coated reactor with antibody insulin | Coated control | Uncoated control |
|---|---|---|---|
| 1 | 9443 (100%) | 75 | 70 |
| 2 | 9115 (96%) | 0 | 0 |
| 3 | 9004 (95%) | 0 | 0 |
| 4 | 8877 (94%) | 0 | 0 |

Example 2: Double Composite Microreactors With Capture Agents Disposed in the In the Matrix 1. 300 $\mu$m alginate beads (internal particle cores) containing porcine islets were produced.

2. The inner cores were coated with a layer of polylysine (0.2% 3.9K polylysine).

3. These coated internal particles were encapsulated to make single composite microreactors of about 500 $\mu$m in diameter. The alginate matrix (in which the internal particles are encapsulated) contained 0.60 $\mu$m latex microspheres (1:1,000 volume/volume ratio of beads-to-alginate) (Bangs Laboratories, Inc., Fishers, Ind.). These microspheres were conjugated with the IgG fraction of dog anti-pig serum (produced by immunizing a dog with pig islets).

4. The single composite microreactors from step 3 were coated with 0.4% 3.9K polylysine to form particles.

5. The coated particles were encapsulated in an alginate supermatrix to form double composite microreactors of about 1200 $\mu$m in diameter.

Example 3: Double Composite Microreactors With Capture Agents Disposed in the Outer Surface the Internal Particle 1. 300 $\mu$m alginate beads (internal particle cores) containing porcine islets were produced.

2. The inner cores were coated with a layer of polylysine (0.2% 3.9K polylysine).

3. The coated internal particles were incorporated into an alginate matrix to provide single composite microreactors about 500 $\mu$m in diameter.

4. The single composite microreactors from step 3 were coated with 0.4% 3.9K polylysine to form particles to which the IgG fraction of dog anti-pig serum has been coupled.

5. The coated particles were encapsulated in an alginate supermatrix to form double composite microreactors of about 1200 $\mu$m in diameter.

Example 4: Implantation of Microreactors Which Include Capture Agents Into Dogs The Microreactors of the Examples can be are introduced into dogs to test their efficacy. Microreactors of a single type, that is, from a single Example listed above can be introduced into a dog. Alternatively, more than one type of microreactor can be introduced into a single dog. For example, microreactors of Examples 2, 3, and 4 can be introduced into a single dog, and if desired distinguished by the size of the microreactor as well as by the size of the internal components. In other words, the size of the latex beads, which are available in a number of diameters, can be used to tag or identify a particular species of microreactor.

Briefly, dog experiments are performed as follows: before implantation the microcapsules are washed in serum free media 4 times with 10×volume and transported to Charles River PharmServices, Southbridge, Mass. Adult mongrel male dogs weighting 20–25 kilograms were used as recipients. Laparotomy is performed through a short 1–2 cm midline abdominal incision. 5–10 ml of microreactors (containing 3–5×$10^4$ porcine islets in total) were suspended in 75 ml of Hanks M199 media and distributed randomly into the peritoneal cavity by catheter. After implantation, the abdominal wall muscles and the skin wound were sutured closed.

The microspheres are left in the dogs for about two weeks, then recovered and the viability of the islet ascertained. Control microreactors were also administered which were similar but did not include capture agents. The dogs received antibiotics and Aleve (naproxen, a nonprescription nonsteroidal anti inflammatory). The dogs received no immunosuppressants.

Example 5: Double Composite Microreactors With Multiple Capture Agents Disposed on an Internal Particle and In the Supermatrix 1. 300 μm alginate beads (internal particle cores) containing porcine islets were produced.

2. The inner cores were coated with a layer of polylysine (0.2% 3.9K polylysine).

3. The coated internal particles were incorporated into an alginate matrix to provide single composite microreactors about 500 μm in diameter. The alginate matrix (in which the internal particles were encapsulated) contained 0.60 μm latex microspheres (1:1,000 volume/volume ratio of beads-to-alginate). The IgG fraction of dog anti-serum was coupled to the latex beads.

4. The single composite microreactors from step 3 are coated with 0.4% 3.9K polylysine to form particles to which the IgG fraction of dog anti-pig serum has been coupled.

5. The coated particles are encapsulated in an alginate supermatrix to form double composite microreactors of about 1200 μm in diameter.

Example 6: Antigen-Release From Microreactors Cultured In Vitro As A Function of Time Microreactors containing a therapeutic source, i.e., porcine islet cells, were incubated in various media at varying temperatures over periods of time in order to determine the rate of antigen release from the microreactors.

Briefly, the antigen release experiments were performed as follows: porcine islet cells contained within alginate microspheres, were cultured on either standard medium (MEM plus 10% heat inactivated horse serum) or in serum free medium (chemically-defined media) at various temperatures (i.e., 26° C. or 37° C.) and the amount of antigens remaining on the surface of the islets were determined over a period of 5 days to 23 days.

The experiments were performed with microreactors containing porcine islets under three different conditions. Group A microspheres were cultured at 37° C. in standard medium; Group B microspheres were cultured at 26° C. in standard medium; Group C microspheres were cultured at 37° C. in serum-free chemically defined medium. At days 5, 14 or 23, an aliquot of microspheres was sampled, andporcine islet cells from each group were released from the microspheres by treatment with EDTA. The islet cells were then mechanically dissociated into single cells or small clusters using a 5 ml pipette, and were centrifuged to form pellets. The cells were washed with PSA (PBS, 1% BSA, 0.1% sodium azide) and resuspended in 50 μl of control or immune sera (containing rat anti-pig IgG). After 30 minutes at 4° C., the islet cells were washed with PBA and incubated in 50 μl of FITC-conjugated goat anti-rat IgG whole molecules (Sigma, St.Louis, Mo.). The amount of FITC-labeled antigens present on the islet cells were measured using a fluorescence activated cell sorter FACStar-Plus™ flow cytometer (Becton Dickinson, San Jose, Calif.). Analysis was done with FAC-Scan™ research software (version 2.1) and the QUIK CAL 138 program. The fluorescence intensity for the control group (unlabeled islet cell) was also measured and the values listed below have been adjusted above background fluorescence levels. The results are presented in Table 1.

This experiment demonstrates that the mean channels of fluorescence intensity of the islet cells dropped approximately eight to sixteen fold from day 5 to day 23.

TABLE 2

Release of Antigen from Microreactors During Pretreatment Incubation Periods

| Time In | Fluorescence (Percent of Initial) | | |
|---|---|---|---|
| Days | Group A | Group B | Group C |
| 5 | 4971 (100%) | 5861 (100%) | 6924 (100%) |
| 14 | 1395 (28.1%) | 1342 (22.9%) | 1518 (21.9%) |
| 23 | 590 (11.9%) | 888 (15.2%) | 425 (6.1%) |

Other Embodiments

Capture agent-related methods of the invention can be used to treat a variety of disorders. These include disorders that result from the defective or insufficient production of a particular substance, e.g., enzyme or hormone, and other disorders, e.g., trauma-related disorders, such as spinal cord injury.

A number of well-characterized disorders caused by the loss or malfunction of specific cells in the body are amenable to implantable device-medicated replacement therapy. For example, in addition to the islets of Langerhans, which can be used for the treatment of diabetes as described above, hepatocytes can be used for the treatment of hepatic failure, adrenal gland cells can be used for the treatment of Parkinson's disease, nerve growth factor (NGF)-producing cells can be used for the treatment of Alzheimer's disease, factors VIII- and IX-producing cells can be used for the treatment of hemophilia, and endocrine cells can be used for the treatment of disorders resulting from hormone deficiency, e.g., hypoparathyroidism.

Moreover, by using recombinant DNA methods to supply a cell which produces a disease product, or encapsulating other tissues, implantable devices can be used to treat patients suffering from chronic pain, cancer (e.g., hairy cell leukemia, melanoma, and renal carcinoma), AIDS (treated by immunological augmentation), Kaposi's Sarcoma (treated by administration of interferon, IL-2, or TNF-α), primary hematologic disorders, patients with long-lasting aplasia, and patients who are myelosuppressed (treated by bone marrow transplantation and aggressive chemotherapy). Implantable devices should also be useful in the treatment of affective disorders, e.g., Huntington's Disease, Duchenne's Muscular Dystrophy, epilepsy, infertility. Implantable devices can also be used to promote wound healing and to treat traumatic, mechanical, chemical, or thermal injuries, e.g., spinal cord injuries, and in wound healing.

Implantation of specific cells can also serve to detoxify, modify, or remove substances from the circulation, e.g., drugs, poisons, or toxins. For example, the implantation of appropriate living cells restores normal physiologic function by providing replacement for the diseased cells, tissues, or organs, e.g., in hepatic encephalopathy (produced by liver disease) or uremia (produced by kidney failure).

In embodiments of the invention, the encapsulated cells can release fairly large molecules, e.g., IgG molecules. In many applications the critical host component which must be excluded is Clq, which has a molecular weight of about 410 kDa. Thus, the molecular weight cutoff will be about 400 kDa and molecules of up to this size can be released. Genetically engineered cells can also be used in the methods of the invention. For example, cells can be engineered to release larger products, e.g., IgG.

In each application, a sufficient number of composite implantable devices, containing the desired living cells, can be implanted into the patient, e.g., surgically or with a syringe. The implantable devices are implanted, e.g., intraperitoneally, for a systemic effect, or into a particular location, e.g., the brain to treat Parkinson's disease, or the spinal cord to chronic pain or treat spinal cord injuries, for a local effect.

The dose of implantable devices to be used is determined initially from results of in vitro studies. In addition, in vivo results in, e.g., mice, rats, or dogs will facilitate more accurate assessment of required doses, as these tests are generally predictive of efficacy in human patients. For example, canine insulin dependent diabetes represents an excellent model of cellular and humoral autoimmunity (Nelson, *Diabetes Spectrum* 5:324–371 (1992))

The implantable devices are intended to remain in the patient with viable donor cells for extended periods of time up to several months or years. However, if it is determined that the donor cells are no longer viable, e.g., by monitoring the patient's blood for a certain level of the protein secreted by the donor cells, it is a simple task to remove the implantable devices and renew the supply of beads in the patient.

Diabetes Mellitus

To treat diabetes, e.g., in a dog or human patient, the implantable beads preferably encapsulate isolated canine or porcine islets or other cells that produce insulin or insulin-like growth factor 1 (IGF-1). Islets are prepared and encapsulated using procedures described above. Insulin secretory activity of the encapsulated cells or islets is determined both in static culture, e.g., expressed per islet volume, and based on the capability of the islets to respond to graded concentrations of glucose. These values are established as described above. Once the insulin secretion activity of a particular batch of encapsulated islets is determined, the proper number of beads can be determined and implanted into a diabetic patient. For example, to treat a human patient that requires 20 to 50 units of insulin per day, the total number of beads should be selected to contain a total of about 1.0 to 2.5 million porcine islets. For beads designed to contain, on average, 30,000 islets/ml of gel, the proper dosage would be beads made from 30 to 85 ml of gel.

Hemophilia

Hemophilia is an X-linked hereditary bleeding disorder caused by Factor VIII or Factor IX deficiency. Recombinant methods have now been successfully used to create Factor VIII- and Factor IX-producing cells as described above. Encapsulation in implantable devices and implantation of such cells according to the present invention can thus be used for an improved treatment for hemophilia.

Hepatic Diseases

Hepatocyte transplantation is useful not only for irreversible hepatic failure, but for several disease processes including hereditary enzyme abnormalities, acute hepatic failure, where the ability of the liver to regenerate can occur, and as a bridge to whole liver transplantation in patients who develop sudden hepatic failure, either because of medical progression or because of rejection-related complications.

Wong and Chang, *Biomat. Art. Cells Art Org.*, 16:731 (1988), have demonstrated the viability and regeneration of microencapsulated rat hepatocytes implanted into mice. Viable hepatocytes were microencapsulated in alginate-poly-(L-lysine) and implanted intraperitoneally into normal and galactosamine-induced liver failure mice. Eight days after implantation in the mice with induced liver failure, the viability of the encapsulated rat hepatocytes increased from 42% to nearly 100%. After 29 days, the viability of the encapsulated hepatocytes implanted in normal mice also increased from 42% to nearly 100%. By contrast, free rat hepatocytes implanted into mice all died within four or five days after xenotransplantation. Implantable devices are well-suited to treat hepatic failure.

Other investigators have shown that microencapsulated hepatocytes continue the synthesis and secretion of many specific proteins and enzymes. Cai et al., *Hepatology*, 10:855 (1989), developed and evaluated a system of microencapsulation of primary rat hepatocytes. Urea formation, prothrombin and cholinesterase activity, the incorporation of titrated leucine into intracellular proteins, and the immunolocation of synthesized albumin were monitored in culture. Despite gradual decreases in some of these activities, the encapsulated hepatocytes continued to function throughout the 35-day observation period. In addition, Bruni and Chang, *Biomat. Art. Cells Art. Org.*, 17:403 (1989),demonstrated the use of microencapsulated hepatocytes to lower bilirubin levels in hyperbilirubinemia. Microencapsulated hepatocytes were injected into the peritoneal cavity of Grunn rats. Bilirubin dropped from 14 milligrams/100 ml to 6 milligrams/100 ml, and remained depressed after 90 days. Again, implantable devices can be used as described above to treat these hepatic diseases.

Parkinson's Disease

Parkinson's disease is a neuronal system disease, involving a degeneration of the nigrostriatal dopaminergic system. Experimental work in both rodents and nonhuman primates has shown that transplantation of fetal tissue containing substantia nigra (dopaminergic) neurons from ventral mesencephalon to dopamine-depleted striatum reinstates near-normal dopamine interinnervation and reduces motor abnormalities. In addition, implantation of adrenal chromaffin cells has been shown to reverse chemically-induced Parkinson's disease in rodents.

Widner et al., *Transplant. Proc.,* 23:793 (1991), reported evidence of fetal nigral allograft survival and function up to 10 months after transplantation and immunosuppression (cyclosporin, azathioprine, and prednisone) in a human Parkinson's patient. Beginning from the second month after the transplantation, they observed a progressive decrease in limb rigidity, increased movement speed in a number of arm, hand, and foot movements, and prolonged "on" periods (greater than 80% increase) after a single dose of L-dopa.

Thus, transplantation of fetal neural tissue, or cells genetically engineered to produce dopamine and nerve growth factors or other neurotropic factors, should have a great potential as a new therapeutic approach in patients with neurological disorders. However, in the case of transplanted xenogeneic donor tissue, rejection would pose a serious problem, even by the combined approach of using an immunoprivileged site and by employing immunosuppressive drugs. Therefore methods of the invention permit a novel approach to this problem, i.e., the delivery of dopamine for the treatment of Parkinson's disease using encapsulated donor tissue harvested from animals or genetically engineered cells.

Alzheimer's Disease

An estimated 2.5 to 3.0 million Americans are afflicted with Alzheimer's disease. The disease is characterized by a progressive loss of cognitive function associated with degeneration of basal forebrain cholinergic neurons. Studies in animals indicate that Nerve Growth Factor (NGF), e.g., brain-derived neurotrophic factor (BDNF) and neurotrophin-3 (NT-3), available from Regeneron and Amgen, respectively, and other neurotropic factors normally act to support the viability and function of these neuron cells, and that continuous infusion of NGF into the ventricles can prevent injury-induced degeneration of cholinergic neurons as described in Williams et al., *P.N.A.S., USA,* 83:9231 (1986). This treatment correlates with improved cognitive function in rodents with memory impairment as described in Fisher et al., *Neurobiol. Aging,* 10:89 (1989).

These studies suggest that implantable devices containing grafts of recombinant or natural NGF-secreting tissue such as astroglial cells or developing skin, can be used to treat patients suffering from Alzheimer's disease.

Gene Therapy

Gene therapy is an approach to treating a broad range of diseases by delivering therapeutic genes directly into the human body. Diseases that can potentially be cured by gene therapy include diseases associated with the aging population such as cancer, heart disease, Alzheimer's disease, high blood pressure, atherosclerosis and arthritis; viral infectious diseases such as acquired immune deficiency syndrome (AIDS) and herpes; and inherited diseases such as diabetes, hemophilia, cystic fibrosis, and muscular dystrophy.

In one particular example, a favored approach for human gene therapy involves the transplantation of genetically-altered cells into patients, e.g., as described Rosenberg, et al., *New Eng. J. Med.,* 323:570–578 (1988). This approach requires the surgical removal of cells from each patient to isolate target cells from nontarget cells. Genes are introduced into these cells via viral vectors or other means, followed by transplantation of the genetically-altered cells back into the patient. Although this approach is useful for purposes such as enzyme replacement therapy (for example, for transplantation into a patient of cells that secrete a hormone that diseased cells can no longer secrete), transplantation strategies are less likely to be suitable for treating diseases such as cystic fibrosis or cancer, where the diseased cells themselves must be corrected. Other problems commonly encountered with this approach include technical problems, including inefficient transduction of stem cells, low expression of the transgene, and growth of cells in tissue culture which can select for cells that are predisposed to cancer.

The methods of the invention are well suited to avoid these problems, because they allow the use of standard human cell lines of, e.g., fibroblast cells, epithelial cells such as HeLa cells, and hepatoma cells such as HepG2, as the implanted cells, rather than requiring the surgical removal of cells from the patient. These cell lines are genetically altered as required by standard techniques and are encapsulated and implanted into the patient. These cell lines are much easier to obtain, culture, and work with than individual patients' cells. Moreover, since the implantable devices prevent the patient's immune system from recognizing and attacking the implanted cells, any human cell lines can be used, making the technique of gene therapy more universally applicable.

Hypoparathyroidism

Acute and chronic symptoms of hypoparathyroidism result from untreated hypocalcemia, and are shared by both hereditary and acquired hypoparathyroidism. The hereditary form typically occurs as an isolated entity without other endocrine or dermatologic manifestations or, more typically, in association with other abnormalities such as defective development of the thymus or failure of other endocrine organs such as the thyroid or ovary. Acquired hypoparathyroidism is usually the result of inadvertent surgical removal of all the parathyroid glands, and is a problem in patients undergoing operations secondary to parathyroid adenoma or hyperplasia. Hypoparathyroidism has been treated in hypocalcemic rats by the administration of microencapsulated parathyroid cells that served as a bioartificial parathyroid. Parathyroid cells can also be encapsulated in implantable devices and used with the methods described herein in administration to animals and human patients.

Osteoporosis

The term osteoporosis covers diseases of diverse etiology that cause a reduction in the mass of bone per unit volume. These diseases can be treated by the administration of implantable devices containing cells that secrete insulin-like growth factor (IGF-1), estrogen in postmenopausal woman to reduce the negative calcium balance and decrease urinary hydroxyproline, androgens in the treatment of osteoporotic men with gonadal deficiency, or calcitonin for use in established osteoporosis.

Reproductive Disorders

There are numerous disorders of the ovary and female reproductive tract that can be treated with progestrogens, estrogens, and other hormones. These include progestrogen, e.g., progesterone, therapy to inhibit pituitary gonadotropins (precocious puberty in girls), and for prophylaxis to prevent hyperplasia in PCOD. Estrogen therapy is used in the treatment of gonadal failure, control of fertility, and in the management of dysfunctional uterine bleeding. Androgens, gonadotropins, and other hormones are used to treat disorders of the testis, e.g., androgen therapy in hypogonadal men, or gonadotropins to establish or restore fertility in patients with gonadotropin deficiency. Accordingly, these diseases can be treated with implantable devices containing the appropriate hormone-producing cells.

Huntington's Disease

Huntington's disease is characterized by a combination of choreoathetotic movements and progressive dementia usually beginning in midadult life. Distinctive for the disease is atrophy of the caudate nucleus and, to a lesser extent, other structures of the basal ganglia (putamen and globus pallidus). Rodent cells that secrete neurotropic factors have been implanted into the brains of baboons that have a condition similar to Huntington's disease and reversed some of the damaged nerve networks that, in Huntington's patients, lead to progressive loss of control over the body. Similarly, Huntington's disease in human patients can be treated by the administration of implantable devices that contain human or recombinant cells that secrete the appropriate neurotrophic factors.

Spinal Cord Injuries

The majority of spinal cord injuries result from damage to the surrounding vertebral column, from fracture, dislocation, or both. Treatment of such injuries involves the administration of nerve growth factors such as ciliary neurotropic. factor (CNTF), insulin-like growth factor (IGF-1), and neurotropic factors, to enhance the repair of the central and peripheral nervous system. Thus, implantable devices containing cells that secrete such factors, either naturally or through genetic engineering, can be used to treat spinal cord injuries.

Mood (or Affective) Disorders

Mood disorders are a group of mental disorders such as schizophrenia characterized by extreme exaggerations and disturbances of mood and affect associated with physiologic (vegetative), cognitive, and psychomotor dysfunctions. Many mood disorders are associated with medical diseases that can be treated with implantable devices containing the appropriate cells such as hypothyroidism, Parkinson's disease, Alzheimer's disease, and malignancies as discussed herein. In addition, it has been shown that the neurotransmitter 5-hydroxyindol acetic acid (5-HIAA), a serotonin metabolite, is reduced in the cerebral spinal fluid of depressed patients. Deficits in other neurotransmitters such as dopamine and γ-aminobutyric acid (GABA) have also been identified in patients with major depression. Therefore, implantable devices containing cells that secrete these neurotransmitter are useful to treat these deficiencies.

Motor Neuron Diseases

Degenerative motor neuron diseases include ALS (see above), heritable motor neuron diseases such as spinal muscular atrophy (SMA), and those associated with other degenerative disorders such as olivopontocerebellar atrophies and peroneal muscular atrophy. These diseases can be treated by administration of implantable devices containing cells that secrete neurotropic factors like brain-derived neurotrophic factor (BDNF), and neurotrophin-3 (NT-3).

Acquired Immunodeficiency Syndrome (AIDS)

AIDS is caused by an underlying defect in cell-mediated immunity due to the human immunodeficiency virus (HIV), and causes persistent constitutional symptoms and/or diseases such as secondary infections, neoplasms, and neurologic disease. Patients can be treated to ameliorate symptoms by immunologic augmentation with implantable devices that contain cells genetically engineered to secrete, e.g., recombinant human IL-2 (to decrease suppressor cell activity resulting in an increased T cell adjuvant activity); or recombinant human INF-γ (macrophage augmentation). AIDS-related tumors such as Kaposi's sarcoma can be treated with encapsulated cells that secrete human interferon-α, interleukin-2 and tumor necrosis factor (TNF).

Amyotrophic Lateral Sclerosis (Lou Gehrig's Disease)

ALS is the most frequently encountered form of progressive motor neuron disease, and is characterized by progressive loss of motor neurons, both in the cerebral cortex and in the anterior horns of the spinal cord, together with their homologs in motor nuclei of the brainstem. ALS can be treated with implantable devices that contain cells that secrete nerve growth factors such as myotrophin, insulin-like growth factor (IGF-1), ciliary neurotropic factor (CNTF), brain-derived neurotrophic factor (BDNF) and neurotrophin-3 (NT-3). Animal studies with these factors (IGF-1 is available from Cephalon, CNTF from Regeneron, and NT-3 from Amgen), have demonstrated that they can stem the degenerative effects caused by nerve damage or disease.

Cancer

In most cases, cancer originates from a single stem cell which proliferates to form a clone of malignant cells. Growth is not properly regulated by the normal biochemical and physical influences in the environment. There is also a lack of normal, coordinated cell differentiation. Cancer cells develop the capacity for discontinuous growth and dissemination to other parts of the body.

Various cancers can be treated according to the invention by the administration of implantable devices containing cells that secrete interferon-α (IFN-α) (for solid tumors, hairy cell leukemia, Kaposi's sarcoma, osteosarcoma, and various lymphomas); recombinant interleukin-2 (IL-2) (for melanoma, renal carcinoma, and Kaposi's sarcoma); tumor necrosis factor (with IL-2 for Kaposi's sarcoma); recombinant human IFN-α and recombinant human colony stimulating factor-granulocyte macrophage (GM-CSF) (for Kaposi's sarcoma); recombinant human INF-γ (for macrophage augmentation); CSF (for aggressive chemotherapy, bone marrow transplantation, priming of leukemic cells to enhance sensitivity to chemotherapy and to support dose intensification); ciliary neurotropic factor (CNTF) and insulin-like growth factor (IGF-1) (for peripheral neuropathies caused by chemotherapy); adrenal gland cells (for pain relief when injected into the lower spine to secrete natural painkillers) and progesterone-producing cells (for palliation in endometrial and breast carcinoma).

Duchenne's Muscular Dystrophy

Duchenne's dystrophy is an X-linked recessive disorder characterized by progressive weakness of girdle muscles, inability to walk after age 12, kyphoscoliosis (curvature of the spine), and respiratory failure after the fourth decade. This disease can be treated by administration of implantable devices containing myoblast cells and growth factors. Myoblasts have been injected into young boys with Duchenne's muscular dystrophy to determine whether the cells can supply a structural protein that is missing. Researchers have observed muscle strength improvement in several of the boys.

Epilepsy

The epilepsies are a group of disorders characterized by chronic, recurrent, paroxysmal changes in neurologic function caused by abnormalities in the electrical activity of the brain. In some forms of focal epilepsy, inhibitory intemeurons appear to be preferentially lost. Treatment with neurotropic factors and other neuropeptides such as has been found effective. Therefore, the implantable devices containing cells secreting these factors can be used to treat epilepsy.

It is to be understood that while the invention has been described in conjunction with the detailed description thereof, that the foregoing description is intended to illustrate and not limit the scope of the invention, which is defined by the scope of the appended claims. Other aspects, advantages, and modifications within the scope of the invention will be apparent to those skilled in the art to which the invention pertains.

All patents and publications referred to herein are hereby incorporated by reference.

Other embodiments are within the claims.

What is claimed is:

1. An implantable device which includes
a source of a therapeutic substance; and
an agent that inhibits release of a non-therapeutic, therapeutic source derived substance from the implantable device,
the non-therapeutic, therapeutic source derived substance being capable of stimulating an immune response against the therapeutic source or implantable device in a recipient host.

2. The implantable device of claim 1 wherein the agent is an antibody or antibody fragment.

3. The implantable device of claim 2 wherein the antibody or antibody fragment is directed against an antigen selected from the group consisting of MHC class I, MHC class II, SLA class I, and SLA class II antigens.

4. The implantable device of claim 2 wherein the antibody or antibody fragment is selected from the group consisting of a human antibody, a humanized antibody, an antibody which is engineered to minimize host response, and an engineered binding protein.

5. The implantable device of claim 1 wherein the source of the therapeutic substance is an islet.

6. The implantable device of claim 1 wherein the source of the therapeutic substance is a cell or a tissue from a pig.

7. The implantable device of claim 5 wherein the cell is a pancreatic islet cell.

8. The implantable device of claim 1 wherein the agent is immobilized to keep it from contacting the source of a therapeutic substance.

9. The implantable device of claim 1, further comprising
a first compartment, said source of said therapeutic substance being disposed in said first compartment; and
a second compartment, said agent being disposed in said second compartment.

10. The implantable device of claim 8 wherein the agent is immobilized within the interior of the device.

11. The implantable device of claim 1, further comprising
a) a compartment comprising an inert bead, and
b) an interior component, said device having an exterior surface,
said agent being coupled to a component of the device selected from the group consisting of said inert bead, a surface of said interior component, and the exterior surface of said device.

12. The implantable device of claim 1, wherein the device is a microcapsule comprising a gel member in which the source of the therapeutic substance is embedded.

13. A composite microreactor which includes:
(a) one, or a plurality, of an internal particle which includes:
(i) pig islet cells as a source of a therapeutic substance;
(ii) an internal particle matrix;
(iii) an internal semipermeable particle coating enclosing the internal particle matrix; and
(b) a super matrix in which the internal particle (or particles) is embedded; and
(c) an outer semipermeable coating of polylysine enclosing the super matrix, the composite microreactor preferably providing a molecular weight cutoff that prevents molecules larger than about 400,000 daltons from coming into contact with the source and having an antibody which reacts with a swine antigen as an agent that inhibits release of a non-therapeutic, therapeutic source derived substance from the microreactor, the non-therapeutic, therapeutic source derived substance being capable of stimulating an immune response against the therapeutic source or microreactor in a recipient host.

14. The composite microreactor of claim 13 wherein the agent is attached to the outer coating of polylysine.

15. The composite microreactor of claim 13 wherein the agent is located within an internal compartment.

16. The composite microreactor of claim 15 wherein the agent is located in an alginate matrix.

17. The composite microreactor of claim 16, wherein the alginate matrix is coated with polylysine.

18. The composite microreactor of claim 16, wherein the agent is bound to beads within the alginate matrix.

19. The composite microreactor of claim 18, wherein the beads are latex beads.

20. The implantable device of claim 13 wherein the agent is an antibody or antibody fragment.

21. The implantable device of claim 20 wherein the antibody or antibody fragment is directed against an antigen selected from the group consisting of MHC class I, MHC class II, SLA class I, and SLA class II antigens.

22. The implantable device of claim 20 wherein the antibody or antibody fragment is selected from the group consisting of a human antibody, a humanized antibody, an antibody which is engineered to minimize host response, and an engineered binding protein.

23. A double composite microreactor which includes:
(1) one, or a plurality, of an internal particle which includes:
(a) a source of a therapeutic substance which is an islet;
(b) an internal particle matrix which contacts the source; and
(c) an internal particle semipermeable coating enclosing the first internal particle matrix;
(2) one, or a pluralty, of a particle which includes:
(a) the internal particle or particles of (1)
(b) a particle matrix in which the internal particle (or internal particles) is embedded; and
(c) a particle semipermeable coating enclosing the particle;
(3) a super matrix in which the particle (or particles) of (2) is embedded; and (4) a super matrix or outer semipermeable coating; and (5) an agent that inhibits release of a non-therapeutic, therapeutic source derived substance from the microreactor, the non-therapeutic, therapeutic source derived substance being capable of stimulating an immune response against the therapeutic source or microreactor in a recipient host.

24. The double composite microreactor of claim 23, wherein the agent is in a different compartment than is the source of a therapeutic substance, or is immobilized to keep it from contacting the source of the therapeutic substance.

25. The double composite microreactor of claim 23, wherein the agent is coupled to the surface of the microreactor or to the surface of a component of the microreactor.

26. The double composite microreactor of claim 23 wherein the agent is an antibody or antibody fragment.

27. The double composite microreactor of claim 26, wherein the antibody or antibody fragment binds an antigen or epitope other than the therapeutic substance released by the source.

28. The double composite microreactor of claim 27 wherein the antibody or antibody fragment is directed against an antigen selected from the group consisting of MHC class I, MHC class II, SLA class I, and SLA class II antigens.

29. The implantable device of claim 26 wherein the antibody or antibody fragment is selected from the group consisting of a human antibody, a humanized antibody, an antibody which is engineered to minimize host response, and an engineered binding protein.

30. A double composite microreactor which includes:

(1) one, or a plurality, of an internal particle which includes:

(a) a porcine islet;

(b) an internal particle matrix which contacts the source; and (c) an internal particle semipermeable polylysine coating enclosing the first internal particle matrix;

(2) one, or a plurality, of a particle which includes:

(a) the internal particle or particles of (1)

(b) a particle matrix in which the internal particle (or internal particles) is embedded; and (c) a particle semipermeable polylysine coating enclosing the particle;

(3) a super matrix in which the particle (or particles) of (2) is embedded; and (4) an agent that inhibits release of a non-therapeutic, therapeutic source derived substance from the microreactor, the non-therapeutic, therapeutic source derived substance being capable of stimulating an immune response against the therapeutic source or microreactor in a recipient host, wherein said agent is a humanized antibody, a human antibody, or an antibody engineered to minimize host response, which binds an SLA antigen.

31. The double composite microreactor of claim 30, wherein the agent is bound to the internal particle coating.

32. The double composite microreactor of claim 30, wherein the agent is disposed within the particle matrix.

33. The double composite microreactor of claim 30, wherein the agent is bound to the particle coating.

* * * * *